United States Patent
Starson et al.

(10) Patent No.: US 11,942,208 B2
(45) Date of Patent: Mar. 26, 2024

(54) FOOD-RECOGNITION SYSTEMS AND METHODS

(71) Applicant: Passio, Inc., Menlo Park, CA (US)

(72) Inventors: Dmitriy R. Starson, Palo Alto, CA (US); James Kelly, Lancashire (GB); Zvi Ashkenazi, Prescott, AZ (US)

(73) Assignee: PASSIO INC., Menlo Park, CA (US)

( * ) Notice: Subject to any disclaimer, the term of this patent is extended or adjusted under 35 U.S.C. 154(b) by 380 days.

(21) Appl. No.: 17/325,475

(22) Filed: May 20, 2021

(65) Prior Publication Data

US 2021/0365687 A1 Nov. 25, 2021

Related U.S. Application Data

(60) Provisional application No. 63/113,688, filed on Nov. 13, 2020, provisional application No. 63/027,501, filed on May 20, 2020.

(51) Int. Cl.
*G16H 20/60* (2018.01)
*G06F 18/243* (2023.01)
(Continued)

(52) U.S. Cl.
CPC ....... *G16H 20/60* (2018.01); *G06F 18/24323* (2023.01); *G06N 3/08* (2013.01);
(Continued)

(58) Field of Classification Search
CPC .... G16H 20/60; G06F 18/24323; G06N 3/08; G06N 3/045; G06N 5/01; G06V 10/82;
(Continued)

(56) References Cited

U.S. PATENT DOCUMENTS 6,307,959 B1   10/2001   Mandelbaum et al.
6,571,024 B1   5/2003   Sawhney et al.
(Continued)

FOREIGN PATENT DOCUMENTS

WO   2018232378 A1   12/2018

OTHER PUBLICATIONS

Salvador, et al., Learning Cross-Modal Embeddings for Cooking Recipes and Food Images, http://im2recipe.csail.mit.edu, 9 pages.
(Continued)

*Primary Examiner* — Fayyaz Alam
(74) *Attorney, Agent, or Firm* — Cozen O'Connor

(57) ABSTRACT

A food-recognition engine can be used with a mobile device to identify, in real-time, foods present in a video stream. To capture the video stream, a user points a camera of the mobile device at foods they are about to consume. The video stream is displayed, in real-time, on a screen of the mobile device. The food-recognition engine uses several neural networks to recognize, in the video stream, food features, text printed on packaging, bar codes, logos, and "Nutrition Facts" panels. The neural-network outputs are combined to identify foods with high probabilities. The foods may be packaged or unpackaged, branded or unbranded, and labeled or unlabeled, and may appear simultaneously within the view of the mobile device. Information about recognized foods is displayed on the screen while the video stream is captured. The user may log identified foods with a gesture and without typing.

26 Claims, 19 Drawing Sheets

(51) Int. Cl.
*G06N 3/08* (2023.01)
*G06V 10/82* (2022.01)
*G06V 20/40* (2022.01)
*G06V 20/68* (2022.01)
*G06V 30/19* (2022.01)
*G06V 30/224* (2022.01)
*G06V 30/412* (2022.01)

(52) U.S. Cl.
CPC .............. *G06V 10/82* (2022.01); *G06V 20/46* (2022.01); *G06V 20/68* (2022.01); *G06V 30/19173* (2022.01); *G06V 30/2247* (2022.01); *G06V 30/412* (2022.01)

(58) Field of Classification Search
CPC .. G06V 20/46; G06V 20/68; G06V 30/19173; G06V 30/2247; G06V 30/412
See application file for complete search history.

(56) References Cited

U.S. PATENT DOCUMENTS

| | | | |
|---|---|---|---|
| 7,613,323 | B2 | 11/2009 | Nister et al. |
| 7,853,072 | B2 | 12/2010 | Han et al. |
| 7,925,049 | B2 | 4/2011 | Zhu et al. |
| 8,345,930 | B2 | 1/2013 | Tamrakar et al. |
| 8,345,988 | B2 | 1/2013 | Shan et al. |
| 8,385,630 | B2 | 2/2013 | Sizintsev et al. |
| 8,391,592 | B2 | 3/2013 | Han et al. |
| 8,439,683 | B2 | 5/2013 | Puri et al. |
| 9,082,402 | B2 | 7/2015 | Yadgar et al. |
| 9,213,558 | B2 | 12/2015 | Tur et al. |
| 2014/0310001 | A1 | 10/2014 | Kalns et al. |
| 2014/0310002 | A1 | 10/2014 | Nitz et al. |
| 2016/0063692 | A1 | 3/2016 | Divakaran et al. |
| 2016/0163037 | A1 | 6/2016 | Dehais et al. |
| 2018/0089540 | A1 | 3/2018 | Merler et al. |
| 2018/0330198 | A1* | 11/2018 | Harary ................. G06V 10/44 |
| 2019/0080207 | A1 | 3/2019 | Frenzy |
| 2020/0380315 | A1* | 12/2020 | Speiser ................ G06F 18/285 |
| 2021/0014461 | A1* | 1/2021 | Kang .................... G06F 3/0488 |
| 2023/0222821 | A1* | 7/2023 | Delp, III ............. G06F 18/2414 382/110 |

OTHER PUBLICATIONS

Puri, et al., Recognition and vol. Estimation of Food Intake Using a Mobile Device, 978-1-4244-5498, IEEE, 8 pages.
Zhang, et al., "Snap-n-Eat": Food Recognition and Nutrition Estimation on a Smartphone, Journal of Diabetes Science and Technology, 2015, vol. 9(3), pp. 525-533.
Kaur et al., Combining Weakly and Webly Supervised Learning for Classifying Food Images, arXiv: 1712.08730v1 [cs.CV], Dec. 23, 2017, 10 pages.
PCT Application No. PCT/US2021/033327, International Search Report and Written Opinion, dated Aug. 16, 2021, 13 pages.

* cited by examiner

FOOD-RECOGNITION SYSTEMS AND METHODS

RELATED APPLICATIONS

This application claims priority to U.S. Provisional Patent Application No. 63/027,501, filed May 20, 2020, and U.S. Provisional Patent Application No. 63/113,688, filed Nov. 13, 2020. Each of these applications is incorporated herein by reference in its entirety.

BACKGROUND

Multiple studies have shown that accurate understanding and tracking of personal nutrition can improve health outcomes, support treatment of diseases like diabetes and cancer, and help with managing weight and weight-related conditions, among other benefits. Currently available tools to help with food tracking include manual diaries, generic questionnaires, web-based apps (e.g., Weight Watchers), and mobile apps (e.g., MyFitnessPal, Lose It, etc.).

SUMMARY

Many applications and tools currently available for nutrition tracking are difficult to use, and therefore do not exhibit high levels of user satisfaction and adherence to tracking. One complaint of people considering nutrition tracking, and those engaged in nutrition tracking, is the difficulty of logging meals and foods they consumed. Specifically, many currently available applications and tools rely on manual entry where users are required to type food names and select from a list of suggestions. Furthermore, these tools frequently require users to manually set the amount of each food by typing in numbers based on estimation of the amounts by the users. Manual entry is tedious and represents a significant reason why users stop tracking their nutrition. Another complaint is that users find it difficult to estimate the nutrition of foods they are about to eat in real time before they consume the food. Accordingly, it would be desirable to be able to point a smart phone or mobile device at a food, or view the food through smart glasses, to see nutritional information in real-time.

The present embodiments address these difficulties by using a mobile device (e.g., smart phone, tablet, smart glasses, etc.) to simplify the process of logging meals and learning about nutrition, thereby making it faster, more engaging, and more reliable for users. In some of the present embodiments, a user logs a meal by pointing a camera of the mobile device at foods they are about to consume, while viewing video from the camera, as displayed in real-time on a screen of the mobile device. The video is processed by the mobile device frame-by-frame to extract useful data such as food names, food amounts, and other information. While viewing the screen, the user can see useful data displayed next to or over recognized food items, and log their entire meal with a simple swipe or gesture. The mobile device processes the video to identify foods, and displays the identified foods on the screen, either accumulated in a list over the foods or in another convenient location. The user may then log the identified foods with a simple gesture (e.g., swiping on the screen, or selecting a check box). The result is food logging that advantageously does not require typing or taking individual photos, and therefore can be completed with less user effort and higher accuracy.

The present embodiments include a food-recognition engine (see the food-recognition engine 1100 in FIGS. 11 and 20) that may be used on a mobile device to advantageously identify, in real-time, foods present in a video stream captured by the mobile device. The food-recognition engine processes frames of the video stream outputted by a camera of the mobile device to simultaneously identify one or more food items present in the frames. Each food item is identified according to one or more of five modalities of food representation commonly present in meal-logging scenarios: visual recognition of food features, text printed on packaging of the food, a bar code printed on the packaging, a logo printed on the packaging, and "Nutrition Facts" information printed on the packaging. Thus, the food-recognition engine advantageously identifies, and supports logging of, foods that are both packaged and unpackaged, branded and unbranded, and labeled and unlabeled, including combinations thereof, that appear simultaneously within the view of the mobile device.

The food-recognition engine may be used to quickly log foods and nutritional information, thereby facilitating accurate tracking of eating habits and adherence to weight-loss diets and other regimens (e.g., low-carb, low-fat, high-protein, low-sugar, etc.). By combining the ability to recognize foods using multiple modalities in one platform, the food-recognition engine reduces the effort required to gather data and obtain quantifiable metrics related to eating and health. This advantage is particularly relevant to dieters, who may already be experiencing increased levels of stress, and thus more likely to quit dieting. Thus, the reduced effort afforded by the present embodiments can help dieters "stick with it", increasing the chances that they successfully replace old eating habits with new ones.

The food-recognition engine may also be used to facilitate decisions about food portions, food selection, and other food-related decisions by recognizing foods in real-time and showing the information to the users in a way that augments the video stream. For example, the food-recognition engine may show food-related information (e.g., calories) over the foods in the video stream, thereby creating a useful augmented reality feature.

Accurate food recognition and automated nutrition tracking with mobile devices are challenged by the inherent complexity of the food domain, i.e., the large variety of foods and drinks that need to be identified, the variety of representations of foods and scenarios in which the foods are consumed, the visual similarity of various foods, the complexities of settings in which people consume foods, and so on. The present embodiments address these challenges, in part, by applying recent advances in machine-learning algorithms and computation techniques, especially for edge devices such as mobile phones. More specifically, each frame of the video is inputted to multiple types of neural networks to repeatedly ensure a high prediction accuracy for a wide variety of foods. These neural networks, including different types of convolutional neural networks (CNNs), may be implemented on mobile processors (e.g., Apple A12 Bionic, Intel Atom, Nvidia Tegra, etc.) and/or co-processors (e.g., GPUs, FPGAs, machine-learning accelerators, etc.) to process each frame in one second (i.e., 1 fps), or less (e.g., 100 ms per frame corresponding to 10 fps, or 17 ms per frame corresponding to 60 fps). Thus, the present embodiments, unlike prior-art food-recognition tools, can advantageously operate on a mobile device without the delays incurred by transmitting images to an external server that processes the images and transmits the results back to the mobile device.

Due to the fast speed at which the frames are processed, the present embodiments can also present results to a user in real-time by creating a continuous overlay of information on the screen. For example, a label identifying a food may be displayed with the video on the screen, either over or next to the corresponding food. The resulting overlaid video stream shows to a user relevant information about the identified foods, in turn enabling the user to log correctly identified foods into a food log by means of simple on-screen gestures, to manually alter the recognition results, or to use the presented information as a feedback mechanism to adjust the position of the mobile device such that the results displayed on the screen changes.

As an example of this feedback mechanism, the user can change the field-of-view of the camera (e.g., by moving the mobile device closer to or farther from the food item), the viewing angle of the food item, or lighting conditions. In turn, these different perspectives of the food may change how the food-recognition engine identifies foods. For example, if the user zooms in too close to a caprese salad, the food-recognition engine is likely to recognize the individual ingredients of the salad ingredients (e.g., tomatoes, basil and mozzarella). On the other hand, when the camera is farther away, the food-recognition engine is more likely to identify a single caprese salad. The user can immediately see the impact of the change based on the predictions displayed on the screen, and therefore quickly learn how to optimally hold the mobile device to obtain video that gives predictions that align with their expectations. Users also gain flexibility on how they want to log complex meals such as based on ingredients or as recipes. This approach is distinctly faster than prior-art approaches that require users to upload individual static images to remote servers and wait for the results to be returned, and which may subsequently require resubmission of photos if the results from the server are not sufficiently accurate.

To assist with nutrition estimation and food logging, some embodiments of the food-recognition engine estimate volumes of one or more identified foods directly from the video stream. Since most types of food are associated with a calorie density (i.e., calories per unit volume), a volume estimate can be utilized to convert the calorie density into a value for calories. Some techniques to determine food volume from images are described in U.S. Pat. No. 8,345,930. However, the present embodiments advantageously estimate volume from only one set of images (depth images and visual images) that form part of the captured video stream, as opposed to multiple images captured from different angles. The present embodiments may use multiple images to produce improved outcomes, but they utilize algorithms that are less computationally intensive and therefore capable of generating results without the requirement of heavy computation and consumption of computing resources typically associated with volume estimation techniques practiced in the art. The term "volume", as used herein, refers to any quantity of food, including mass (e.g., grams, serving size), weight (e.g., pounds, ounces), and volume (e.g., cubic centimeters, liters, fluid ounces, cups). Volume estimation may also be used to differentiate between various sizes of packaged foods, such as separating an 8-ounce cup of milk from a 12-ounce cup of milk, or a 12-ounce bottle of soda from a 24-ounce bottle of soda.

One aspect of the present embodiments is the realization that confidence levels of a food detected in a sequence of frames of the video stream forms a time series that can be used to improve the classification accuracy, as compared to the confidence level returned by the last frame of the sequence. Accordingly, some of the present embodiments use time-series data across frames of captured video data to improve classification accuracy over prior-art techniques based on individual images.

Another aspect of the present embodiments is the realization that the motion of a mobile device generates video that captures food items from different perspectives. In some cases, this motion is intentional on the part of the user. However, even when a user intends to hold the mobile device stationary, some residual motion still occurs. The changing perspectives that result from camera motion can improve food classification by increasing the likelihood that the food-recognition engine will recognize (i.e., accurately classify) foods in at least some of the various perspectives. This concept is similar to the artificial augmentation of data used to train neural-network classifiers, where multiple "variations" of a training image (e.g., rotations, scales, linear distortions, etc.) are used to train a classifier to improve its classification accuracy.

In embodiments, a food-recognition method includes inputting each frame, of a plurality of frames of a video stream, into a multiple-object detector to obtain (i) a bounding box identifying where each food item, of one or more food items, appears within said each frame, and (ii) a predicted multiple-object class identifying said each food item with a multiple-object probability. The food-recognition method also includes, for each bounding box: (i) cropping said each frame into a cropped frame based on said each bounding box, (ii) inputting the cropped frame into a classifier to obtain one or more predicted classifier classes identifying said each food item with corresponding one or more classifier probabilities, and (iii) determining a food identity of said each food item based on the predicted multiple-object class, the multiple-object probability, the one or more predicted classifier classes, and the corresponding one or more classifier probabilities. The food-recognition method also includes outputting the food identity. The multiple-object detector may be a binary multiple-object detector trained to find food and draw bounding boxes each distinct food object present in the view of the mobile device.

In other embodiments, a food-recognition system includes a processor, a memory communicably coupled to the processor, and a food-recognition engine that includes a multiple-object detector and a classifier. The food-recognition engine is implemented as machine-readable instructions that are stored in the memory and, when executed by the processor, control the food-recognition system to input each frame, of a plurality of frames of a video stream, into the multiple-object detector to obtain (i) a bounding box identifying where each food item, of one or more food items, appears within said each frame, and (ii) a first predicted class identifying said each food item with a first probability. The food-recognition engine also controls the food-recognition system to, for each bounding box: (i) crop said each frame into a cropped frame based on said each bounding box, (ii) input the cropped frame into the classifier to obtain a second predicted class that identifies the corresponding food item with a second probability, and (iii) determine a food identity of the corresponding food item based on the first predicted class, the second predicted class, the first probability, and the second probability. The food-recognition engine also controls the food-recognition system to output the food identity.

The video stream may be displayed on the screen of a mobile device, and the food identity may be displayed on the screen with the video stream. The plurality of frames may include views of the one or more food items taken from different angles. For example, the video stream may be outputted by a camera that moves around the one or more food items as it captures the one or more food items. Alternatively or additionally, the plurality of frames may include views of the one or more food items taken from different distances. For example, the video stream may be outputted by a camera that moves toward or away from the one or more food items as it captures the one or more food items. In some embodiments, the frames of the video stream are inputted sequentially to the multiple-object detector, i.e., in the same order in which they were captured.

DETAILED DESCRIPTION

Figure 1:
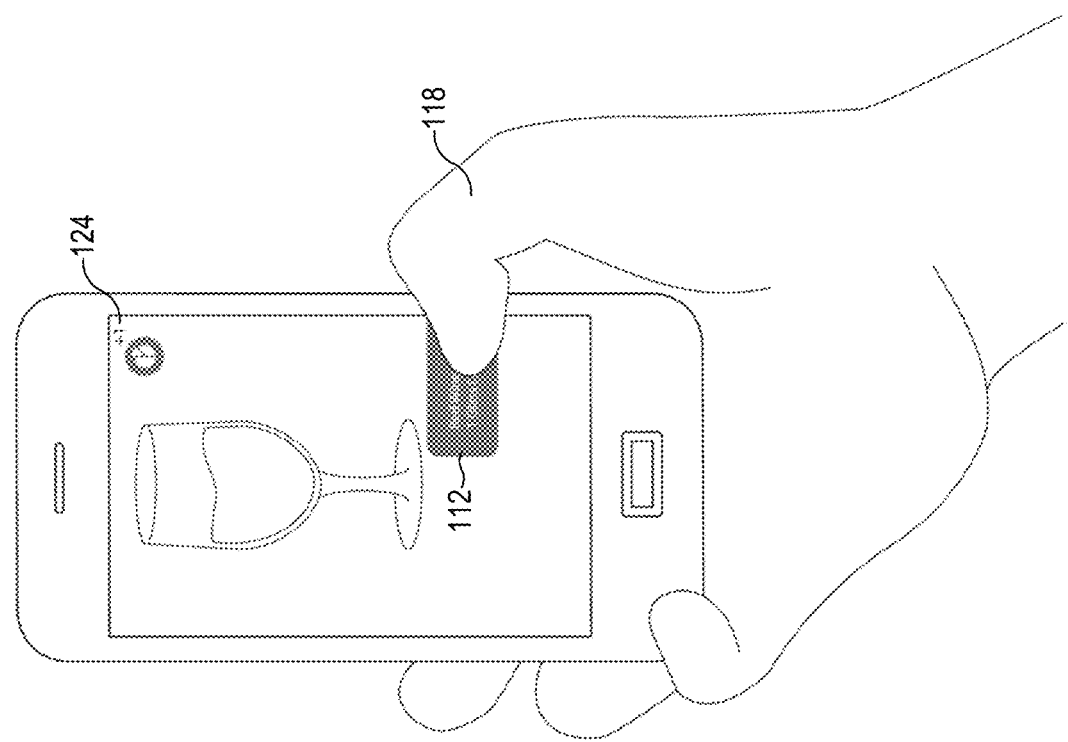
FIG. 1 shows a mobile device identifying a food item from a video stream, in embodiments.
Figure 1:
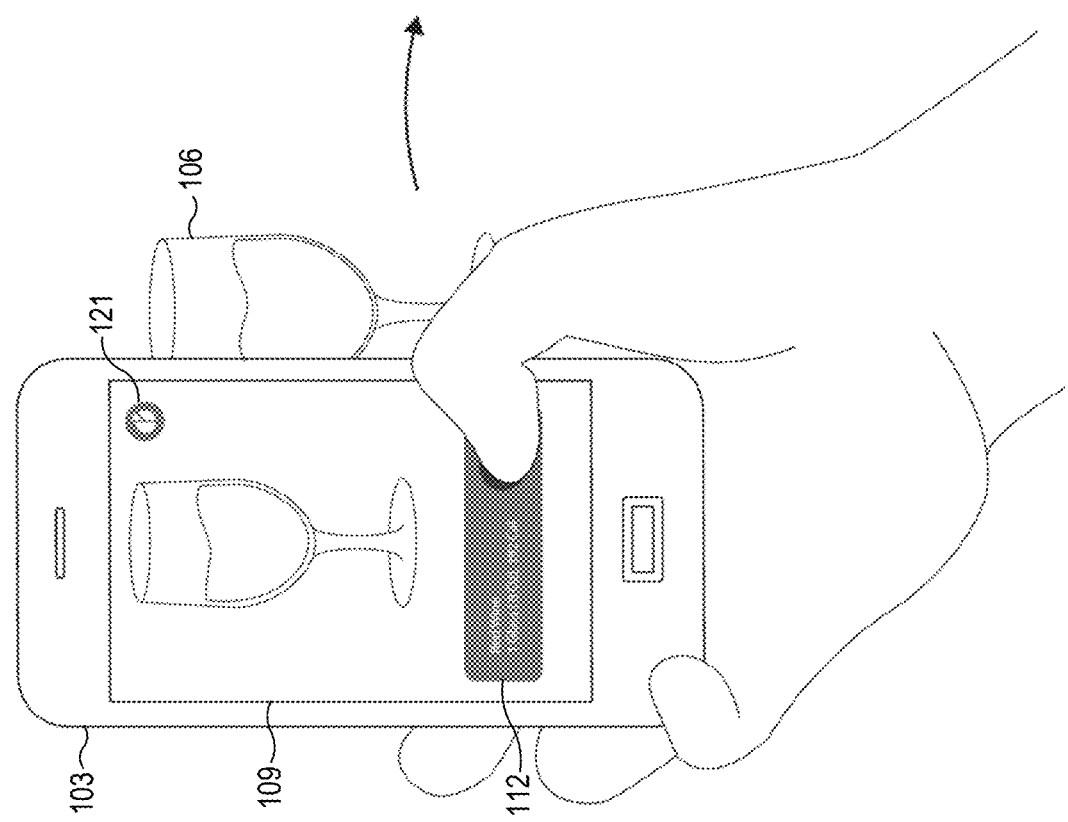

FIG. 1 shows a mobile device 103 identifying a food item 106 from a video stream that is captured by a camera integrated into the mobile device 103 and displayed on a touchscreen 109 of the mobile device 103. The mobile device 103 includes a memory that stores a food-recognition engine (see the food-recognition engine 1100 in FIGS. 11 and 20) implemented as machine-readable instructions, and a processor that executes the food-recognition engine to identify the food item 106 from frames of the video stream (see the food-recognition engine 1900 in FIG. 20). The food-recognition engine identifies the food item 106 as a particular food or drink, a type of food or drink, a size (e.g., serving size, mass, volume, etc.), nutritional information (e.g., calories, proteins, sugars, fats, etc.), and other identifying information. While FIG. 1 shows the food item 106 as a glass of red wine, the food item 106 may be any kind of food or drink. Furthermore, while FIG. 1 shows only a single food item 106, the food-recognition engine can identify multiple food items simultaneously from each image of the video stream. The food-recognition engine may also use a container (e.g., the glass in FIG. 1) or food packaging (e.g., a logo, text, or universal product code (UPC) displayed on a food box, container, wrapper, etc.) to help identify the food item 106.

The food-recognition engine uses a plurality of machine-learning models to identify the food item 106 from the video stream. In the present discussion, these machine-learning models are presented as pre-trained artificial neural networks. However, other types of machine-learning models may be used instead (e.g., random forests, support vector machines, etc.). The pre-trained neural networks are stored in the memory of the mobile device 103, and are used by the food-recognition engine (i.e., on the mobile device 103) to predict both an identity of the food item 106 and an estimated accuracy, or confidence level, of the predicted identity. As discussed in more detail below, some of these neural networks are convolutional neural networks that process the frames of the video stream and include classifiers. While many of the examples presented herein utilize five neural networks, it should be understood that not all five are always needed. Accordingly, some embodiments of the food-recognition engine utilize less than five neural networks. Similarly, the food-recognition engine may utilize more than five neural networks without departing from the scope hereof.

The mobile device 103 also includes a camera (e.g., see the camera 2004 in FIG. 20) that generates the video stream. The food-recognition engine displays the video stream in real-time on the touchscreen 109 of the mobile device 103. A user watching the real-time video stream on the touchscreen 109 and seeing real-time food identities (as predicted by the food-recognition engine) overlaid on the video stream can adjust how the mobile device 103 is positioned so that the camera receives a different view of the food item 106. The different view is processed by the food-recognition engine and may lead to a different prediction. The overlaid identity is updated accordingly, and displayed with each frame of the video stream. Typically, the video stream will have a frame rate between 30 and 60 frames-per-second (fps). However, the video stream may have a different frame rate (e.g., less than 30 fps or greater than 60 fps) without departing from the scope hereof. In embodiments, the video stream has a frame rate of 1 fps or higher. In some embodiments, the touchscreen 109 is replaced with a non-touchscreen display, wherein the user interacts with items on the display via an input device (e.g., a keyboard or mouse).

When the food-recognition engine identifies the food item 106 with sufficient accuracy (i.e., the confidence level is above a threshold), the food-recognition engine controls the mobile device 103 to display, on the touchscreen 109, an identity notification 112 indicating to the user one or more of the identity, size, nutritional content, and confidence level determined by the food-recognition engine. The identity notification 112 may display additional information without departing from the scope hereof. In the example of FIG. 1, the identity notification 112 indicates that the food item 106 is an eight-ounce glass of red wine having 192 calories.

The food-recognition engine may be configured to log foods by any type of user action, or automatically without any user action. For example, the user may swipe the identity notification 112 on the touchscreen 109 (e.g., with a finger 118) to confirm the identity, as shown in FIG. 1. In response, the food-recognition engine adds the food item 106 to a food log (e.g., see the food log 2026 in FIG. 20). As another example of a user action, the user may give a verbal command (e.g., via a microphone of the mobile device 103) to log food, such as by speaking the word "Log". The user can access the food log by, for example, pressing a food-log icon 121 displayed on the touchscreen 109. Upon adding the food item 106 to the food log, the food-log icon 121 is modified with a food-log number 124 indicating a total number of food items that have been added to the food log during the current logging session.

Figure 2:
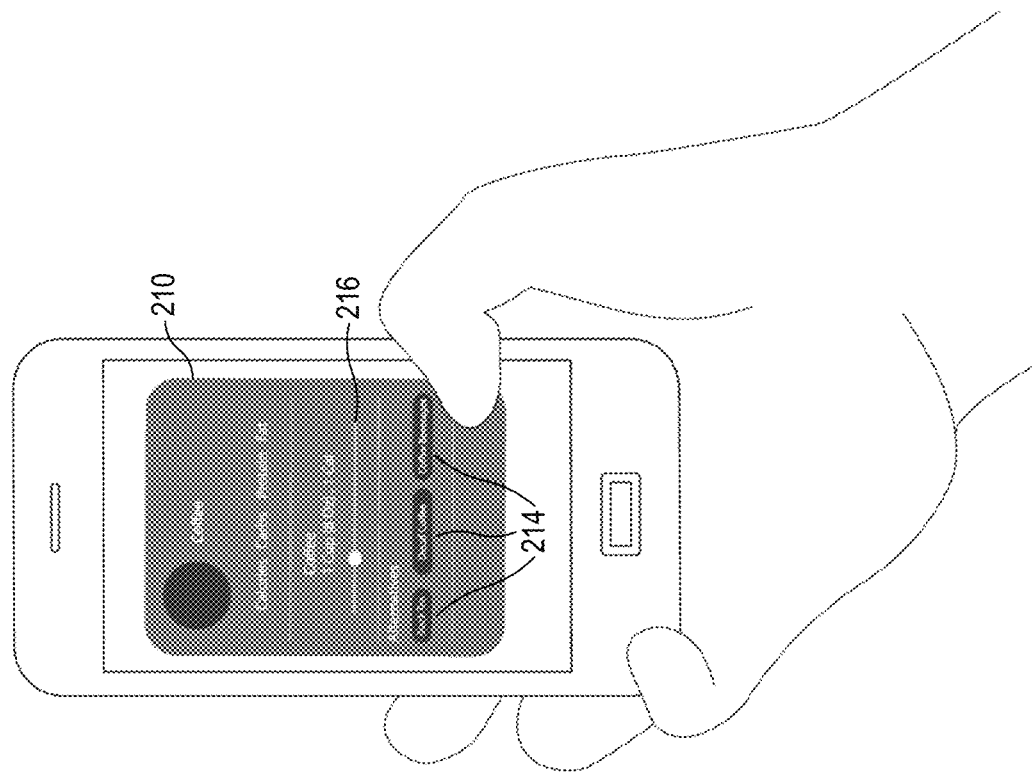
FIG. 2 shows the mobile device of FIG. 1 identifying another food item 206, in an embodiment.
Figure 2:
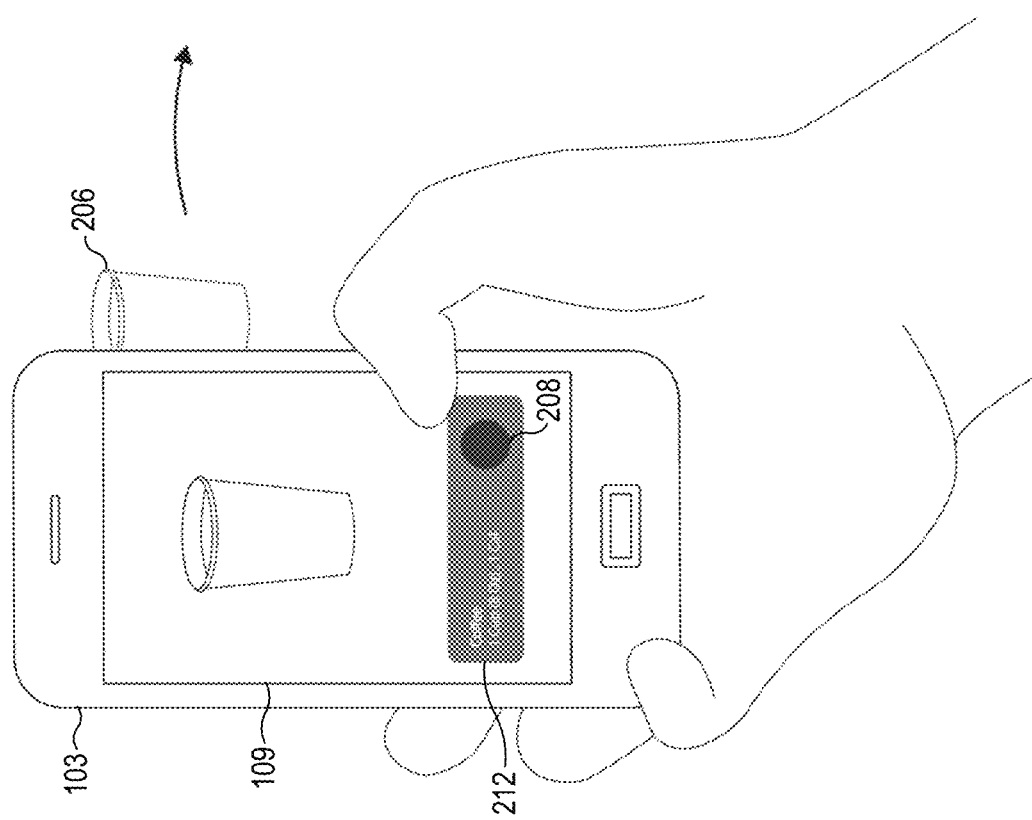

FIG. 2 shows the mobile device 103 of FIG. 1 identifying another food item 206. As shown in a resulting identity notification 212 displayed on the touchscreen 109, the food-recognition engine identified the food item 206 as an eight-ounce cup of coffee having approximately one calorie. The user may press a feature button 208 in the identity notification 212 or tap on the identity notification 212 to bring up an editor card 210 displayed over the video stream. Via the editor card 210, the user can manually change one or more of the food identity, volume, and nutritional information. In this case, the editor card 210 includes a slider bar 216 that the user can move to change the estimated volume of the coffee, and a list of alternatives 214 to coffee that the user can select to modify the identity determined by the food-recognition engine. The alternatives may be selected to account for visual similarity of various foods. For example, black coffee may appear similar to black tea, in which case it may be helpful to show "black tea" as an alternative 214. The user can then select an alternative 214 with one tap, enabling logging of black tea without the need to manually search for black tea or to continue to move the phone in an attempt to get the recognition engine to recognize black tea. The alternatives 214 also allow the user to "drill down" to more detailed results even when the food-recognition engine produces correct results. For example, one of the alternatives 214 could be decaffeinated coffee, which is a more detailed record of coffee.

Although not shown in FIG. 2, the editor card 210 may allow the user to select additional ingredients not appearing in the video stream. For example, the editor card 210 may allow the user to manually select or input a quantity of sugar that the user knows is in the coffee. The food-recognition engine can then update the nutritional information of the coffee based on the user's input. Similarly, if the food-recognition engine identifies milk in the coffee, the editor card 210 may allow the user to manually select a type of milk (e.g., skim, cream, soy, etc.) from which the food-recognition engine can update the nutritional information accordingly. This functionality allows the user to modify the predictions from the neural networks in situations where the food-recognition engine cannot accurately predict the identity of the food item 206. The editor card 210 may also include a "confirm" or "log" button that adds the modified food identity to the food log.

Figure 4:
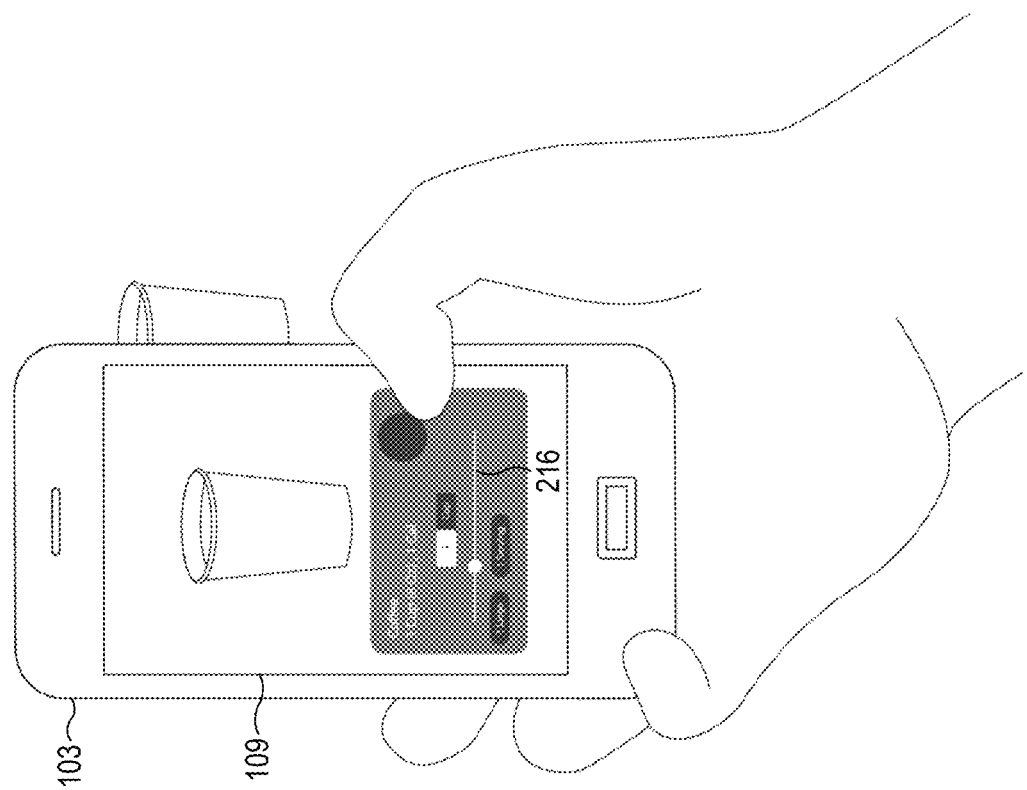
FIG. 4 shows how a user can adjust a slider to edit a food quantity, in an embodiment.
Figure 3:
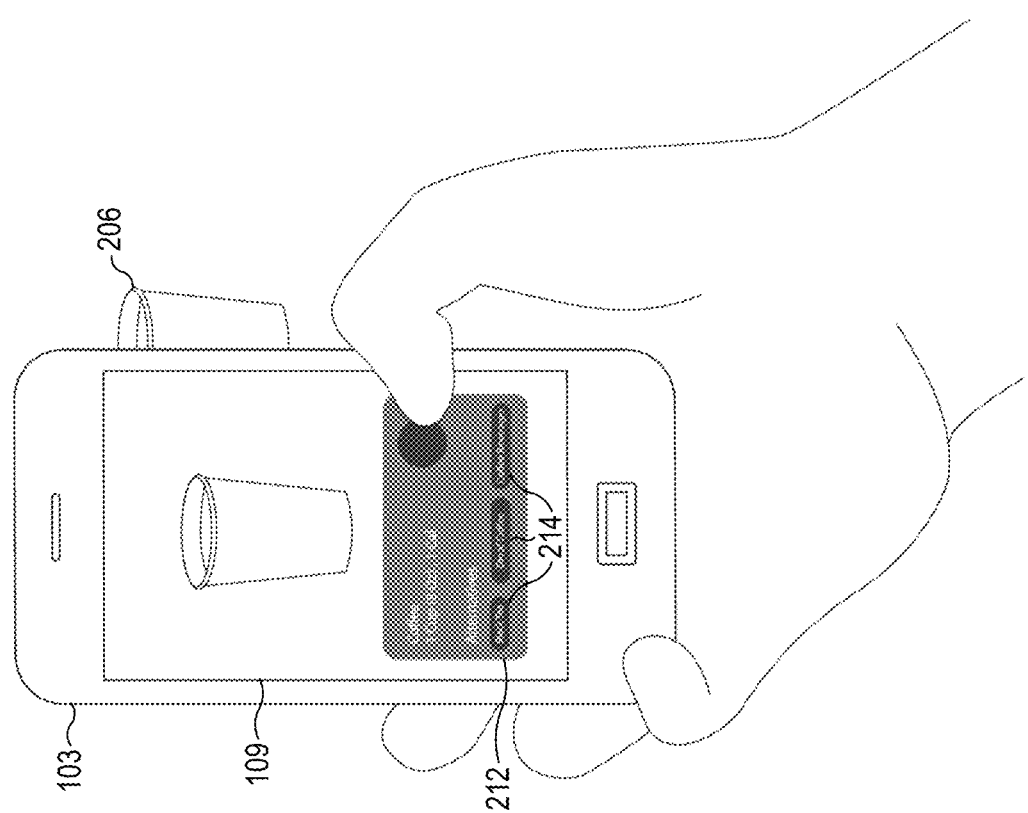
FIG. 3 shows how a user can select an alternative food identity displayed in an identity notification, in an embodiment.

FIGS. 3 and 4 show how some or all components of the editor card 210 may be shown in the identity notification 212 so that the user can access these components without having to tap on the identify notification 212 to bring up the editor card 210. In the example of FIG. 3, the alternatives 214 are shown in the identity notification 212, allowing the user to select an alternative 214 with their finger. In the example of FIG. 4, the slider 216 is shown in the identity notification 212, allowing the user to edit the food quantity by sliding their finger across the touchscreen 109. Other components of the editor card 210 may be shown in the identity notification 212 without departing from the scope hereof.

The exemplary functionality shown in FIGS. 2-4 advantageously allows the user to log foods without typing and without the need to go to a different window or exit the recognition mode. This eliminates the tedious process of searching for food items via typing food names and separately adjusting their amounts. Furthermore, the functionality shown in FIGS. 2-4 uses a database stored in the memory of the mobile device 103 (e.g., see the memory 2008 in FIG. 20) that associates recognition results with information such as nutritional information and alternatives. Alternatively, the database may be stored external to the mobile device 103 (e.g., in the "cloud,"), and accessible by the mobile device 103 via a wireless connection. Since different foods may look similar, this association advantageously allows the use of a taxonomy, i.e., a hierarchical organization of foods, based on a set of criteria such as visual similarity, that links a visually-identified food with possible alternatives (e.g., see the food hierarchy 1400 in FIG. 14 below). For example, "black coffee" may be associate with "decaf black coffee", "black coffee", "black tea", and "black coffee with sugar", among other alternatives 214. This use of a taxonomy advantageously (i) allows typing-free logging of foods with a higher precision than is possible in the prior art, and (ii) eliminates a common problem of computer vision models that frequently confuse similar looking items.

Figure 5:
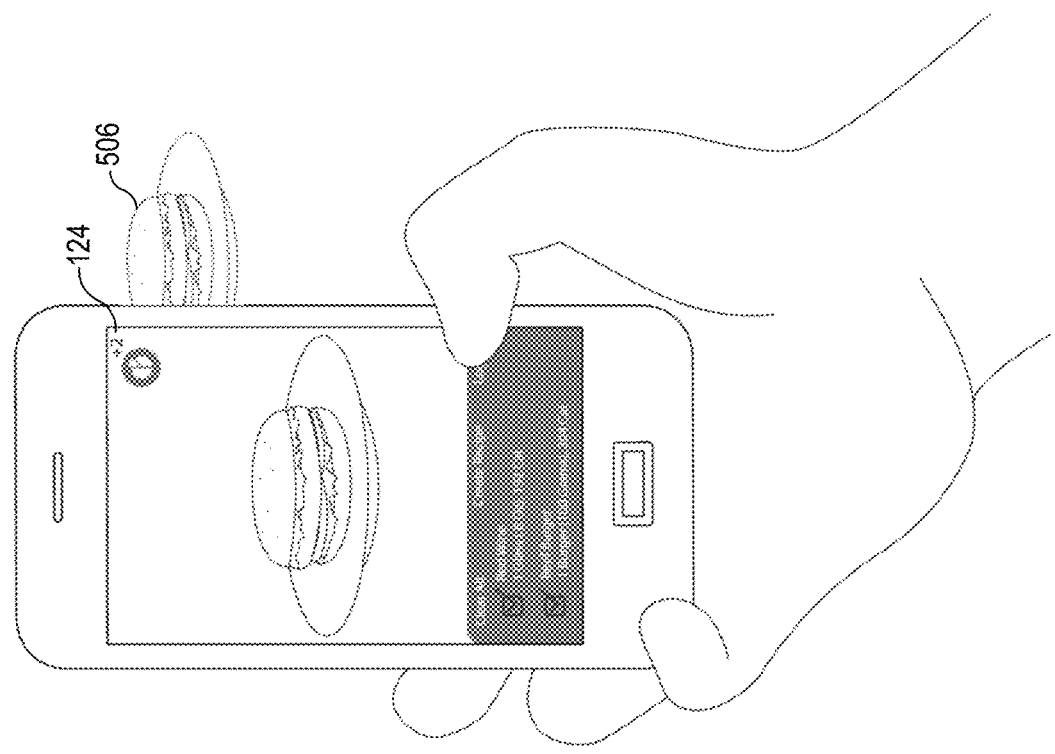
FIG. 5 shows the mobile device of FIG. 1 additionally identifying a second food item, in an embodiment.
Figure 5:
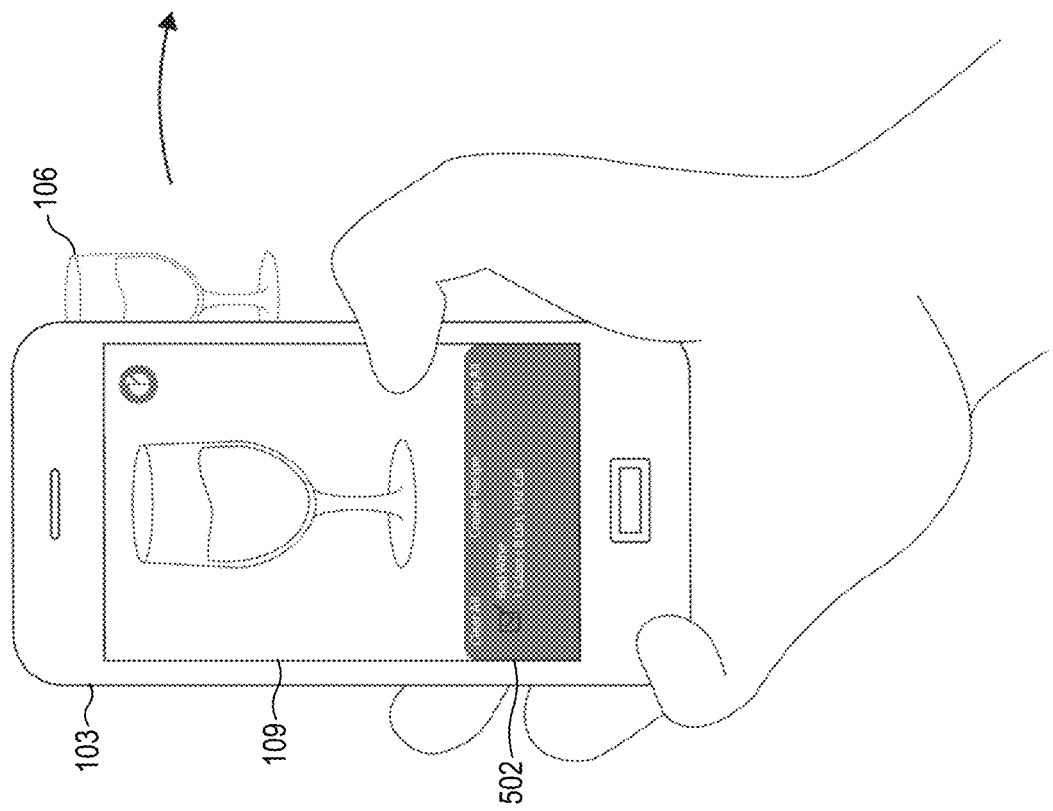

FIG. 5 shows the mobile device 103 of FIG. 1 additionally identifying a second food item 506. In this example, the food-recognition engine displays on the touchscreen 109 a notification tray 502 instead of the identity notification 112. Each food identity determined by the food-recognition engine is listed in the notification tray 502 with a check-box that the user may check to confirm the identity, or uncheck to reject the identity. As the mobile device 103 is moved to capture video of another food item 506, the notification tray 502 continues to display food identities no longer appearing in the video, and may be enlarged to display new food identities. Thus, in FIG. 5, the notification tray 502 continues to display "Red Wine" even as the mobile device 103 is moved to only capture "Beef Burger" (i.e., the food item 506). FIG. 5 also shows the user selecting a "Log All" button displayed in the notification tray 502. This user action adds to the food log all food identities in the notification tray 502 that are checked. In this case, the food-log number 124 is updated to reflect the presence of two items in the food log.

The exemplary operation shown in FIG. 5 allows a user to move the mobile device 103 over a plate of food, and other nearby food items, and log all recognized foods at once. This functionality provides an advantageous way to log meals, as compared to alternatives known in the art. Instead of requiring the user to log foods one-by-one, a user may simply move or swipe the mobile device 103 over an array of foods, and the food-recognition engine will automatically add those foods into a tray showing the recognition results. In some embodiments, all recognized foods are marked with a check, and the user may log all checked foods with one affirmative action, such as tapping on "Log All". The food-log icon 124 may be updated according to the number of checked foods to indicate a total number of food items in the food log.

The food-recognition engine described herein supports recognition of foods at multiple frames per second, thereby allowing a large number of foods (e.g., 3 to 10 foods, or more) to be collected within one motion of the mobile device 103 lasting just a few seconds. For example, logging of the glass of wine (i.e., the food item 106) and beef burger (i.e., the food item 506) can be completed in under one second, thus providing a unique and highly advantageous way for tracking meals.

Also shown in FIG. 5 is a "Create Recipe" button that the user may press to combine multiple checked food items in the notification tray 502 into one combined food item. The user may subsequently name the combined food item and add it to the food log. This functionality provides the user with a convenient way to include foods that have several components combined together, such as salads. This functionality also allows the user to associate ingredients of a recipe that collectively appear visually different from the individual ingredients. For example, a smoothie may look different than the individual fruits, vegetables, and other ingredients commonly combined to make the smoothie.

Figure 6:
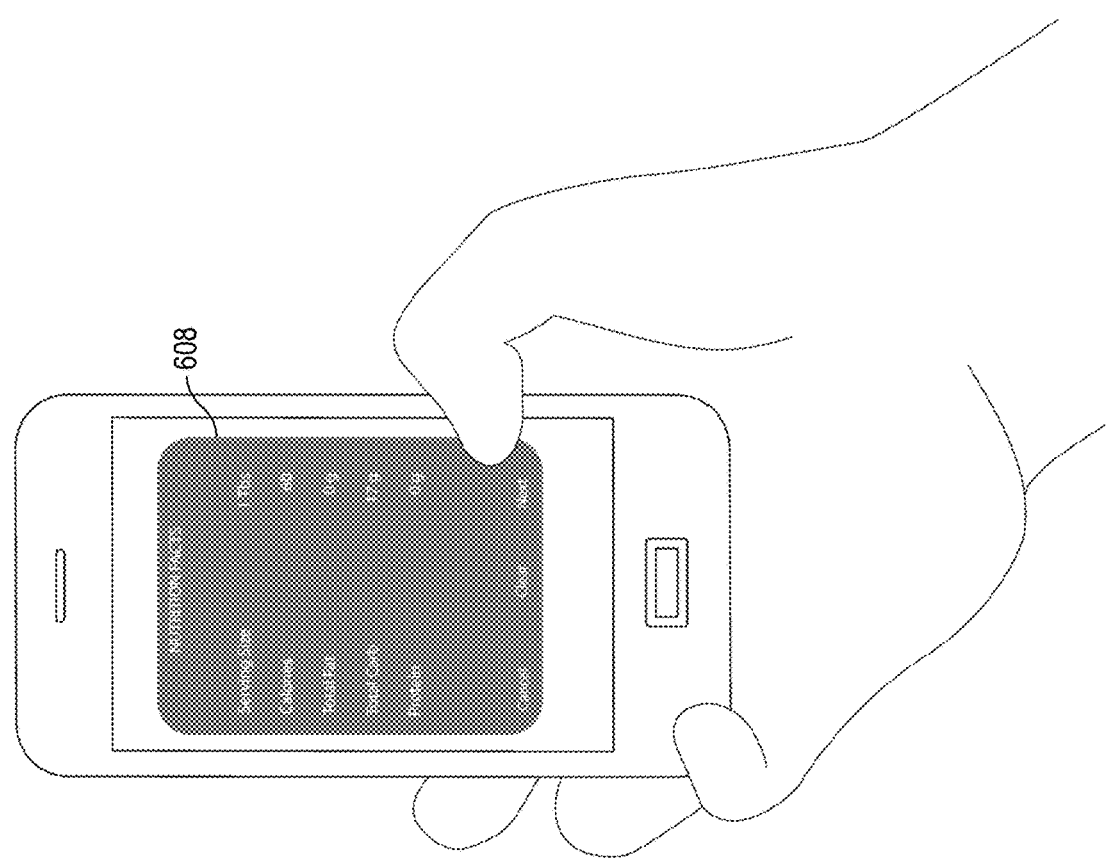
FIG. 6 shows the mobile device of FIG. 1 identifying a food item based on nutritional facts printed on packaging of the food item, in an embodiment.
Figure 6:
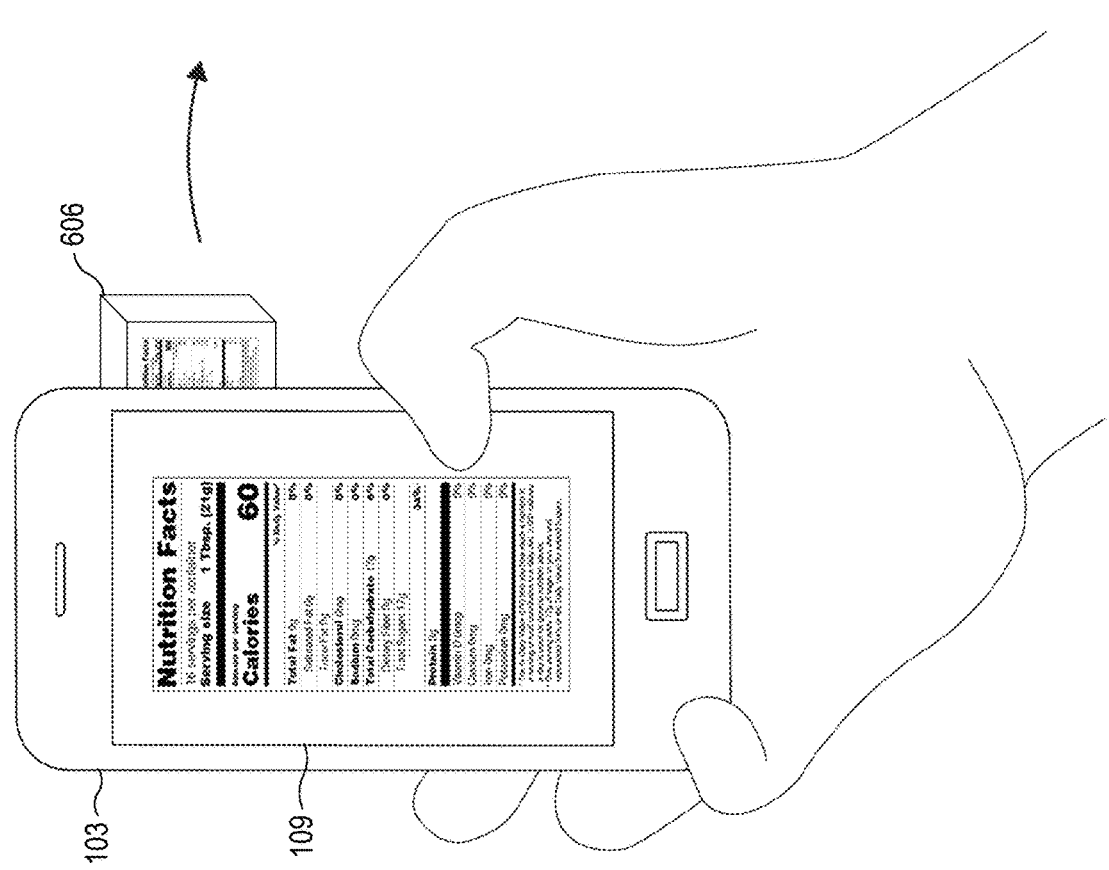

FIG. 6 shows the mobile device 103 of FIG. 1 identifying a food item 606 based on nutritional facts printed on packaging of the food item 606. Here, the food-recognition engine uses optical character recognition (OCR) to find a "Nutrition Facts" box in the video stream. When such a box is found, additional text in the "Nutrition Facts" box is used to determine the nutritional information. As shown in FIG. 6, a message 608 may be shown to allow the user to confirm that the nutritional information was correctly read from the packaging, and update any information that was incorrectly read. Although not shown in FIG. 6, the user may additionally give the food item 606 a name and add it to the food log with the given name.

Figure 7:
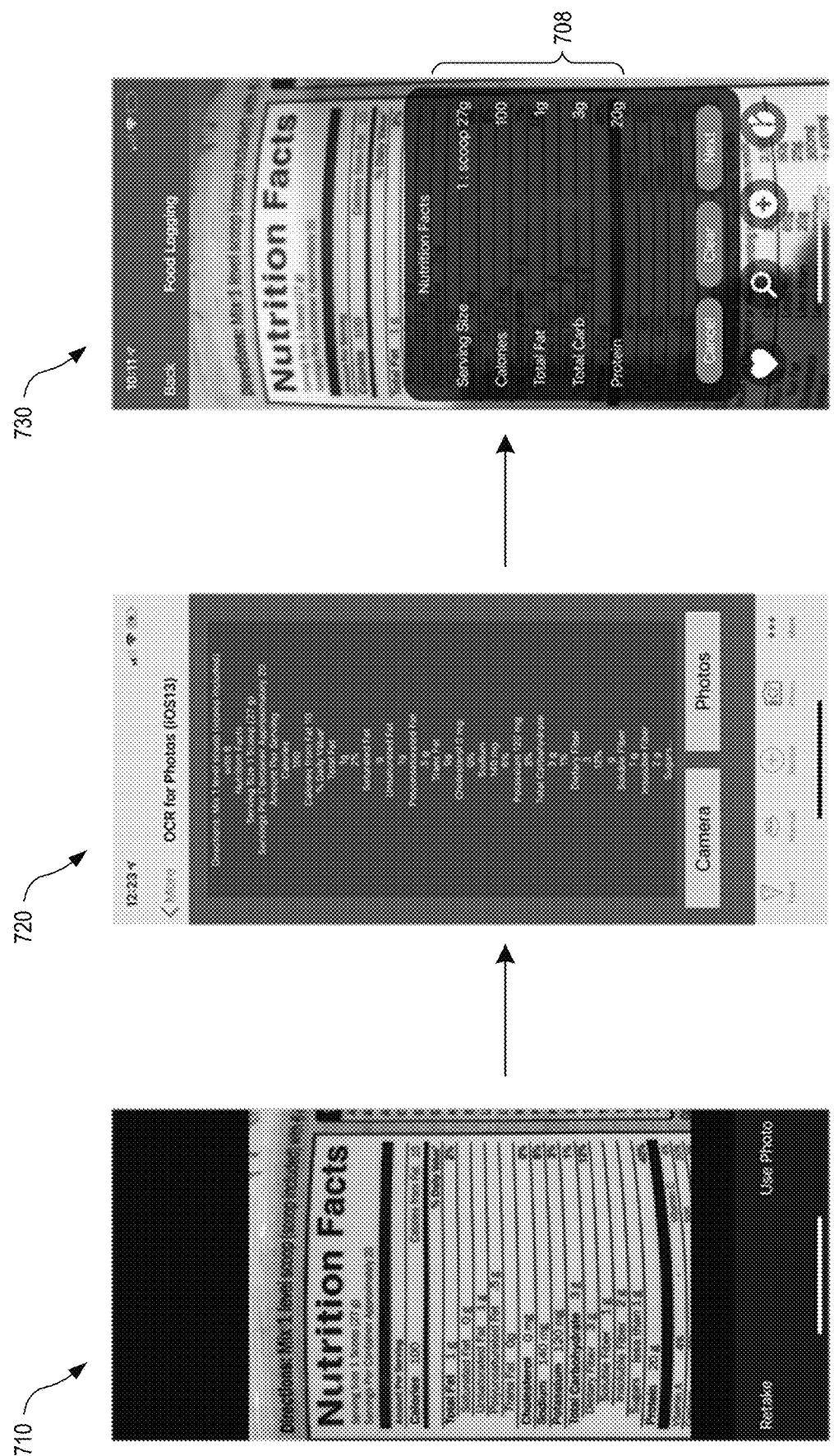
FIG. 7 is a demonstration of a mobile device using OCR to recognize nutritional facts, in an embodiment.

FIG. 7 is a demonstration of a mobile device using OCR to recognize nutritional facts. A screenshot 710 shows an image of a "Nutrition Facts" box that appears on packaging of a food item, as captured by a camera of the mobile device. A screenshot 720 shows the text recognized by the OCR. A screenshot 730 shows a window 708 with the nutritional facts that were recognized from the text. In some embodiments, the user may, via the window 708, edit the recognized nutritional facts if some of the numbers where captured incorrectly. The user may also clear the results and run the OCR-based food recognition process one or several more times until satisfactory results are achieved.

Figure 8:
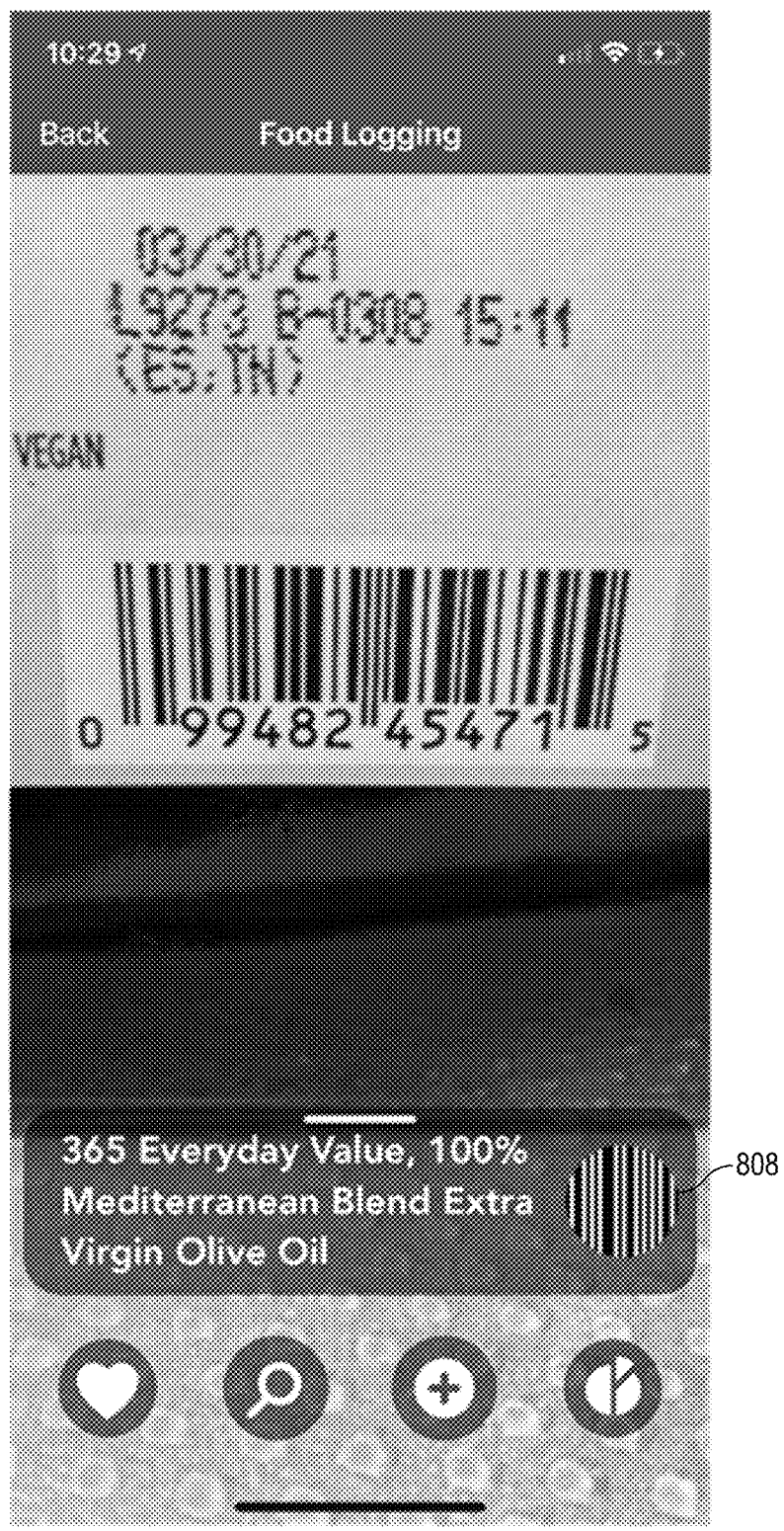
FIG. 8 is a screenshot of a mobile device recognizing a packaged food item based on a barcode that appears on the packaging, in an embodiment.

FIG. 8 is a screenshot of a mobile device recognizing a packaged food item based on a barcode that appears on the packaging. The screenshot includes an image of the barcode, as captured by a camera of the mobile device. The food-recognition engine may process the image to obtain the 10-digit UPC code that appears in the image. The food-recognition engine may then search a database with the UPC code to retrieve the name of the food item. The food-recognition engine may also retrieve corresponding nutritional information. In FIG. 8, the food identity retrieved from the database is displayed in a window 808.

OCR-based and barcode-based food recognition are two ways in which the present embodiments support food logging without requiring the user to type or search for additional information on their mobile device. Although the functionality shown in FIGS. 6-8 is useful by itself, additional benefits to the user come from combining this modality with others disclosed herein (e.g., visual recognition of non-packaged foods, etc.). This is because complete nutrition logging cannot be reduced to logging only packaged foods with nutrition labels and barcodes, as most people also eat foods that either come unpackaged (e.g., fresh produce) or are served without the packaging (e.g., at a restaurant).

Figure 9:
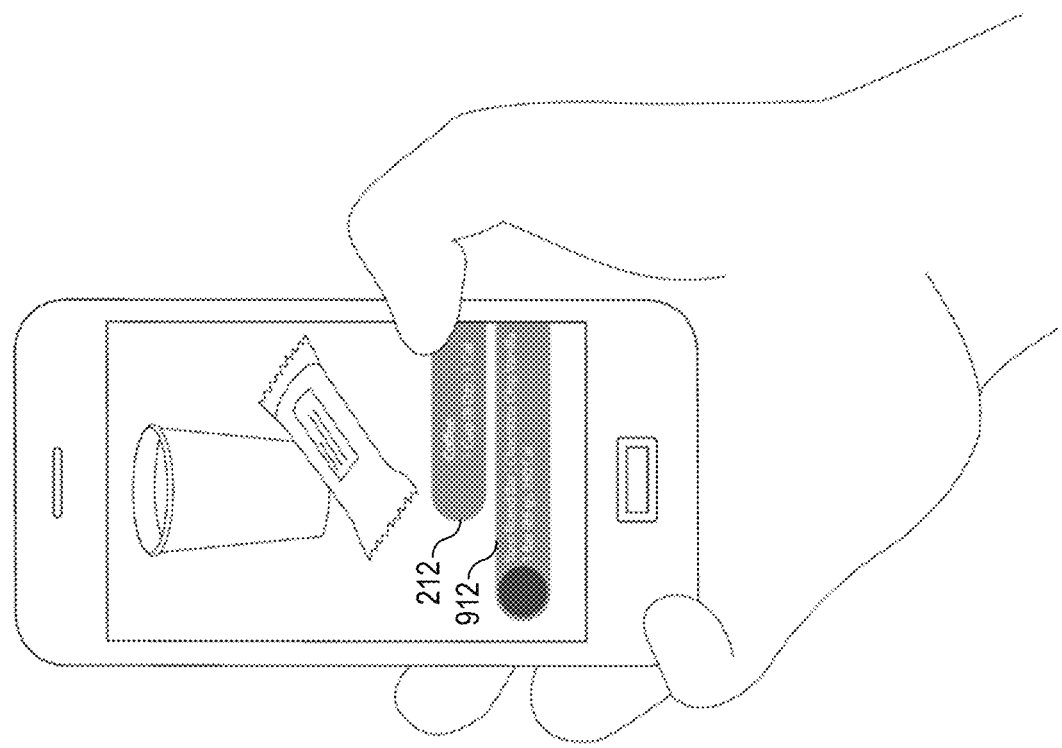
FIG. 9 shows the mobile device of FIG. 1 identifying two food items and at the same time, in embodiments.
Figure 9:
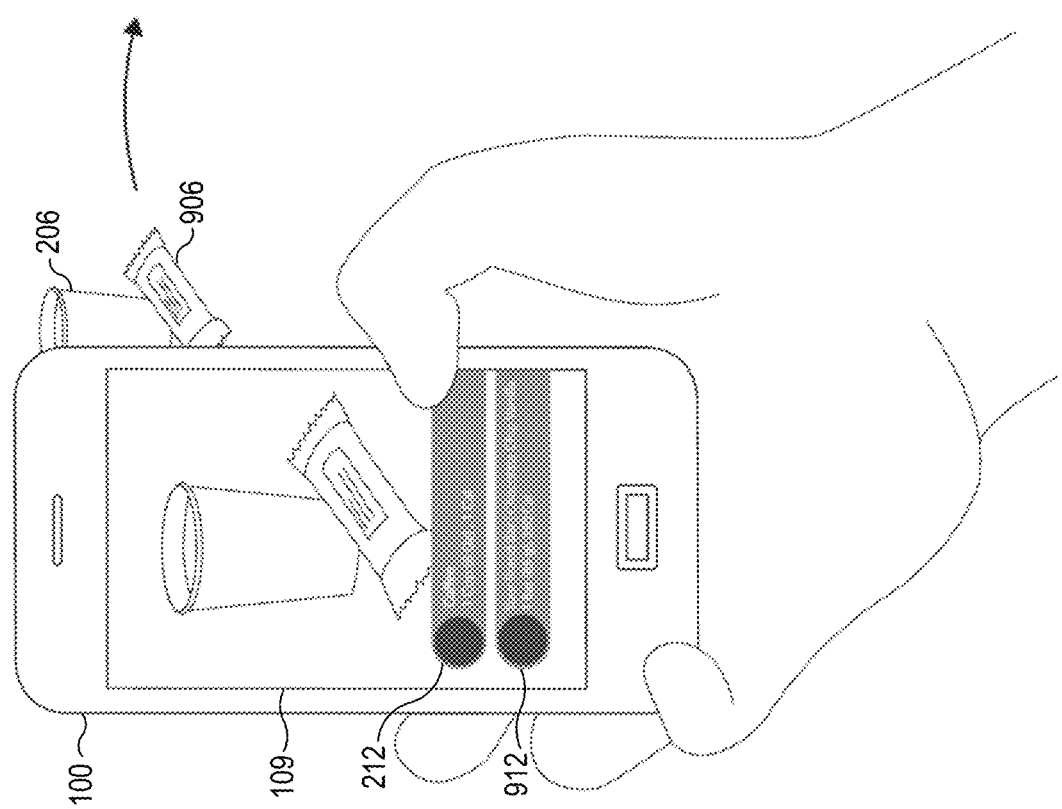

FIG. 9 shows the mobile device 103 identifying two food items 906 and 206 at the same time. As shown in a second identity notification 912 displayed on the touchscreen 109, the food-recognition engine identified the second food item 906 as a chocolate chip vanilla bar with approximately 250 calories. Similar to the identity notification 212, the user may swipe the identity notification 912 to add the identified food to the food log. As described in more detail below, the food-recognition engine can identify the second food item 906, and determine its size and nutritional information, from text printed on its packaging and processed using OCR, a bar code printed on the packaging, or a UPC code printed on the packaging. In some cases, the food-recognition engine can identify the second food item 906 by recognizing a logo on the packaging, and requiring the user to select a more detailed alternative associated with the brand of the logo.

The simultaneous recognition shown in FIG. 9 relies on the same concept of using multiple neural networks concurrently within the food-recognition engine, and may lead to better user experience in situations where users have multiple unique items in front of them. The exemplary functionality shown in FIG. 9 is similar to that shown in FIG. 5 where multiple recognized foods are aggregated in a tray. However, in FIG. 9 the recognized foods are accumulated in the bottom right of the screen and users may choose to log the items by swiping the items to the right. Another benefit of the food-recognition system that is shown in FIG. 9 is simultaneous recognition of foods using multiple modalities. Specifically, one food item is recognized purely via visual recognition whereas the second is a packaged food recognized via optical character recognition (see OCR engine 1115 in FIG. 11). As described in more detail below, the food-recognition engine can simultaneously identify foods using other combinations of modalities.

Figure 10:
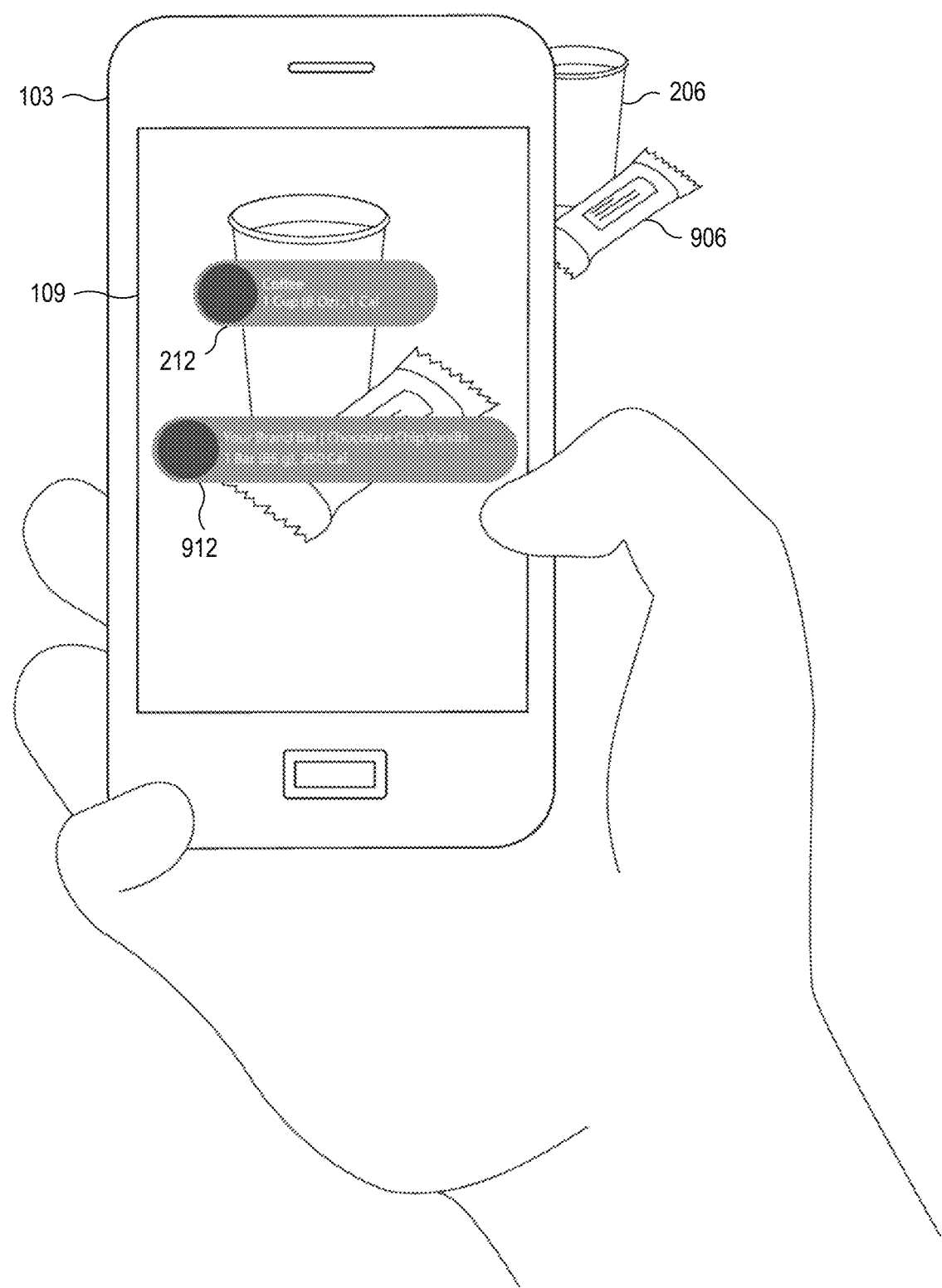
FIG. 10 shows the mobile device 103 of FIG. 1 identifying two food items at the same time, and displaying identity notifications and next to their respective foods, in an embodiment.

FIG. 10 also shows the mobile device 103 identifying two food items 906 and 206 at the same time, but displaying identity notifications 212 and 912 next to their respective foods in the video stream. In this example, each food item is identified with a surrounding bounding box (not shown), and the corresponding identity notification is positioned relative to coordinates (e.g., center coordinates) of the surrounding bounding box.

Figure 11:
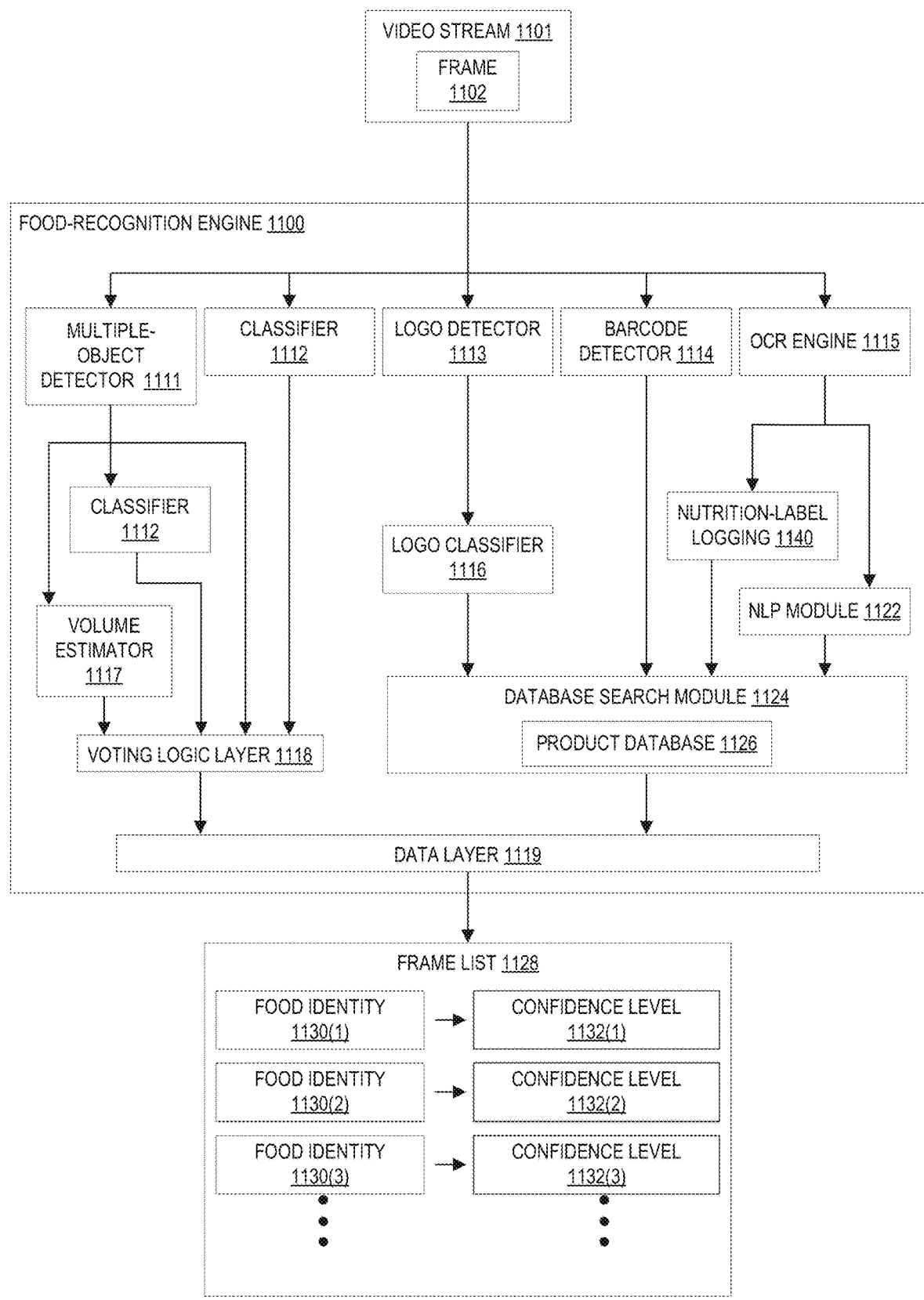
FIG. 11 is a block diagram of a food-recognition engine that may be used with the mobile device shown in FIGS. 1-10, in embodiments.

FIG. 11 is a block diagram of a food-recognition engine 1100 that may be used with the mobile device 103 shown in FIGS. 1-10. The food-recognition engine 1100 may be implemented as computer code, i.e., machine-readable instructions that, when executed by a processor, implement the functionality discussed herein (see FIG. 20). The food-recognition engine 1100 includes a multiple-object detector 1111 that processes frames 1102 of a video stream 1101. In some embodiments, the multiple-object detector 1111 is implemented as a convolutional neural network (CNN), such as R-CNN, Fast R-CNN, Faster R-CNN, YOLO (You Only Look Once), SSD (Single-Shot MultiBox Detector), or another type of machine-learning-based algorithm for real-time object detection. In any case, the multiple-object detector 1111 outputs a list of bounding boxes identifying where within the frame 1102 each detected food item is located. For each bounding box (i.e., detected object), the multiple-object detector 1111 also outputs a predicted multiple-object class and a corresponding multiple-object probability. The multiple-object detector 1111 is pre-trained to recognize a plurality of multiple-object classes, of which the predicted multiple-object class is one. The predicted multiple-object class is the one of the plurality of multiple-object classes having the highest probability, and is therefore the most likely candidate for the true identity of the food item appearing in the cropped frame.

Figure 12:
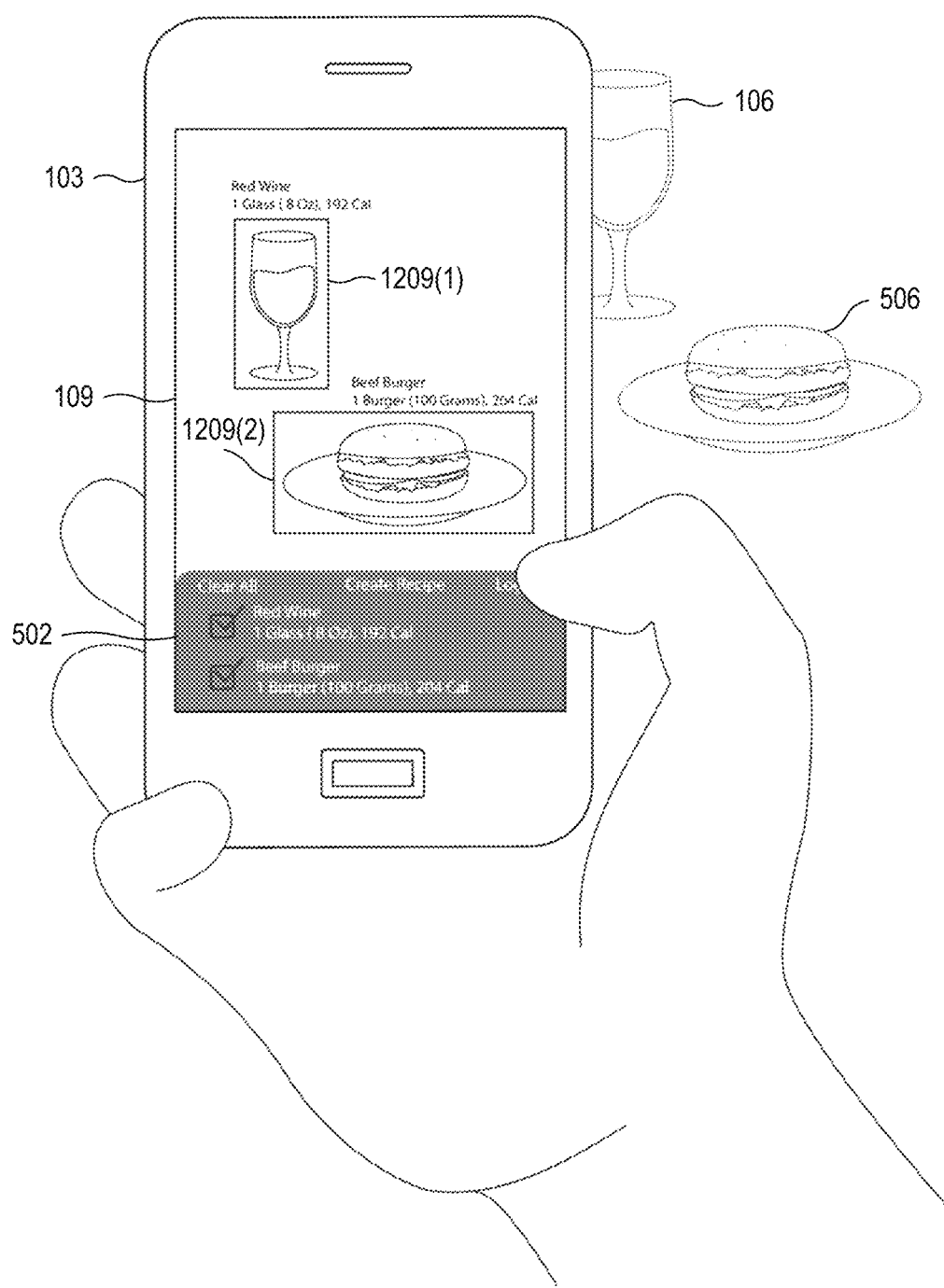
FIG. 12 shows how a multiple-object detector generates a bounding box around each identified food in a frame.

FIG. 12 shows how the multiple-object detector 1111 generates a bounding box 1209 around each identified food in a frame 1102. In this case, the multiple-object detector 1111 generates a first bounding box 1209(1) that identifies where in the frame 1102 the food item 106 (i.e., the glass of wine) appears, and a second bounding box 1209(2) that identifies the food item 506 (i.e., the beef burger) appears. In FIG. 12, the bounding boxes 1209 are displayed on the touchscreen 109. However, this display of bounding boxes is optional and may, for example, be turned on or off by the user. While the example of FIG. 12 shows two bounding boxes 1209, the multiple-object detector 1111 will generate one bounding box 1209 for each identified food, and no bounding box 1209 when no food can be identified in the frame 1102.

The food-recognition engine 1100 also includes a classifier 1112 that provides a second prediction for each food item found by the multiple-object detector 1111. For each bounding box returned by the multiple-object detector 1111, the frame 1102 is cropped into a cropped frame that is inputted to the classifier 1112. The classifier 1112 may be a CNN (e.g., MobileNet, ResNet), or another type of neural network, pre-trained to classify each cropped frame according to a plurality of classifier classes. The classifier 1112 returns a feature vector storing one or more classifier probabilities corresponding to one or more predicted classifier classes of the plurality of classifier classes. The predicted classifier class with the highest classifier probability is also referred to herein as the top predicted classifier class. In some embodiments, the number of multiple-object classes is different from the number of classifier classes. For example, the multiple-object detector 1111 may be pre-trained to classify into 1,000 multiple-object classes, while the classifier 1112 may be pre-trained to classify into 10,000 classifier classes. In other embodiments, the multiple-object detector 1111 and classifier 1112 are pre-trained with the same number of classes.

One aspect of the present embodiments is the realization that the additional classification performed by the classifier 1112 can improve prediction accuracy, as compared to using only the multiple-object detector 1111. The reason for this improvement is that the classifier 1112 is trained to recognize only a single object appearing in an inputted image, while the multiple-object detector 1111 is trained to recognize multiple objects appearing in the image. Cropping of the frame 1102 removes background pixels that only add noise, and therefore may improve the accuracy of the classifier 1112.

The food-recognition engine 1100 also contains a voting logic layer 1118 that aggregates the predicted multiple-object class and probability, and the one or more predicted classifier classes and classifier probabilities, to generate the best prediction for a food identity 1130 for the one food item located within each bounding box. For example, if the predicted multiple-object class and the top predicted classifier class are the same, then the voting logic layer 1118 may equate the food identity 1130 to this class. The voting logic layer 1118 may also determine a food-identity confidence level 1132 for the food identity 1130 based on the multiple-object probability and the highest classifier probability. For example, when the predicted multiple-object class and the top predicted classifier class are the same, then the voting logic layer 1118 may set the food-identity confidence level 1132 equal to the larger of the multiple-object probability and the highest classifier probability, the average of the multiple-object probability and the highest classifier probability, or another number mathematically derived from the multiple-object probability and the highest classifier probability.

If the predicted multiple-object class is different from the top predicted classifier class, the voting logic layer 1118 may equate the food identity 1130 with the multiple-object class, and set the food-identity confidence level 1132 equal to the multiple-object probability level, when the multiple-object probability is greater than the highest classifier probability. Alternatively, the voting logic layer 1118 may equate the food identity 1130 with the top classifier class, and set the food-identity confidence level 1132 equal to the highest classifier probability, when the highest classifier probability is greater than the multiple-object probability. The voting logic layer 1118 may implement other ways of determining food identities 1130 and their confidence levels 1132 without departing from the scope hereof. For example, the multiple-object probability may be weighted higher or lower than the one or more classifier probabilities if it is known (e.g., through testing) that on average the classifier 1112 performs worse or better than the multiple-object detector 1111.

Figure 13:
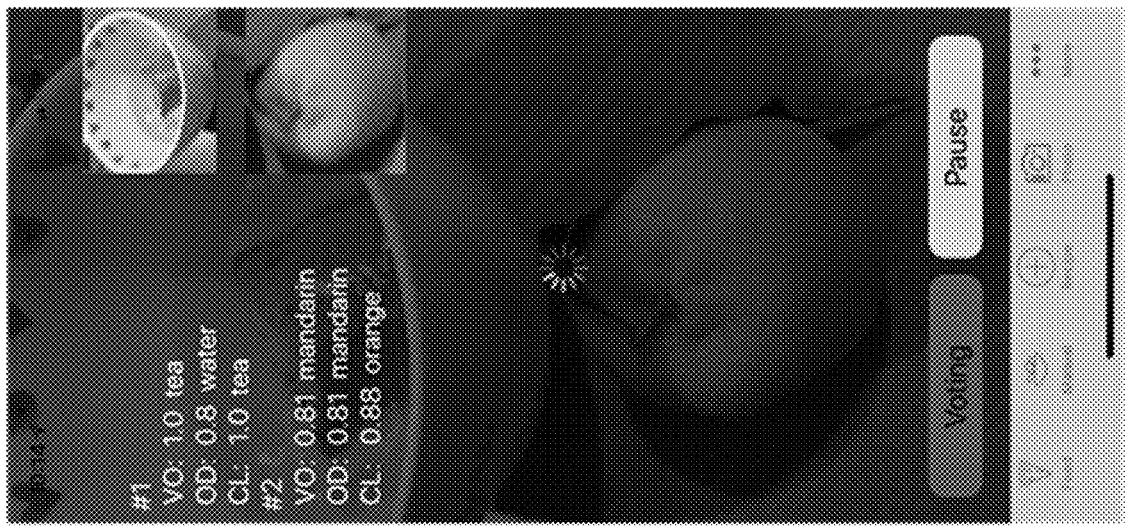
FIG. 13 shows two screenshots of a mobile device that illustrate examples of how a voting logic layer combines predicted classes and probabilities to generate food identities, in an embodiment.
Figure 13:
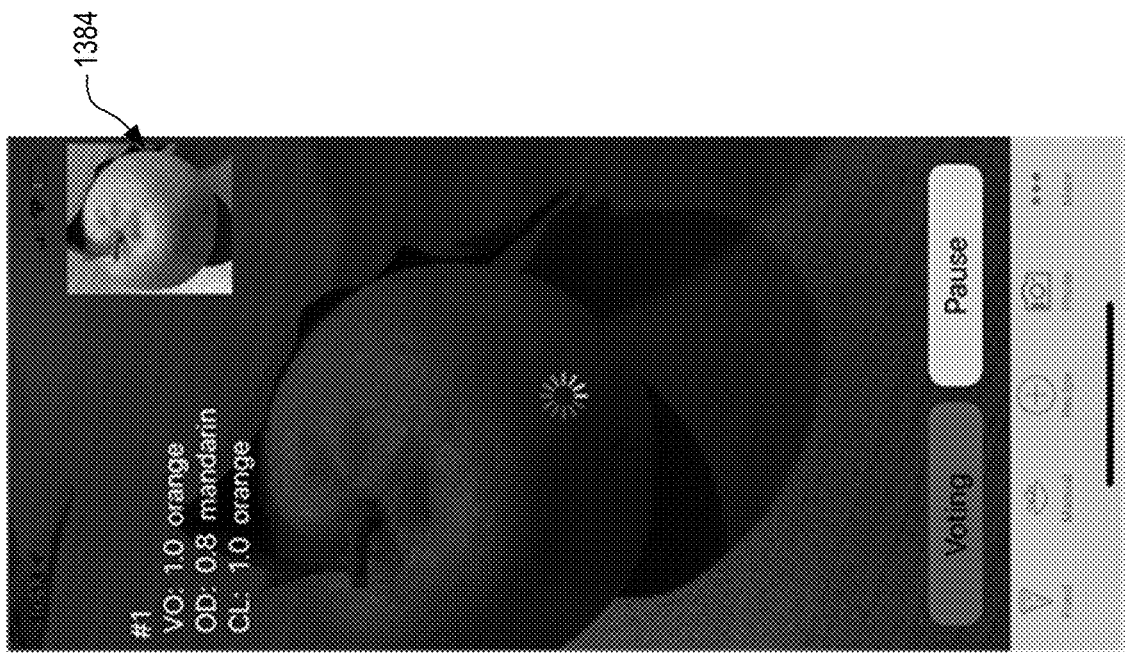

FIG. 13 shows two screenshots of a mobile device that illustrate examples of how the voting logic layer 1118 combines predicted classes and probabilities to generate food identities 1130. In a first screenshot 1380, only one food item is recognized. The multiple-object detector 1111 (OD) processes the full image to classify the food item as a mandarin with a multiple-object probability of 0.8. The full image is cropped into a cropped image 1384, which the classifier 1112 (CL) processes to classify the food item as an orange with a classifier probability of 1.0. The logic layer (VO) selects the output of the classifier 1112 as the food identity 1130, as it has a higher probability than the multiple-object probability.

The functionality shown in a second screenshot 1382 is the same as the first screenshot 1380, except that two food items have been identified. In the first cropped result (labeled as #1), the voting logic layer 1118 identified this food item as "tea" since the classifier (CL) probability of 1.0 was higher than the multiple-object (OD) probability of 0.8. The OD result was water. The second cropped result (labeled as #2) is mandarin. In this case, the OD probability is less than the CL probability, indicating that these probabilities are given different weightings when deciding the final result. Accordingly, the logic layer 1118 may use one or more formulas to decide what final result to select. Furthermore, results displayed to users may be further improved by combining multiple frames via time sequences, as described below. Additionally, the user's experience may be improved by showing alternatives next to recognition results. In the case of FIG. 11, for example, it may be advantageous to show both mandarin and orange and let the user select one or the other via the display method shown in FIG. 2.

For each bounding box of the frame 1102, the voting logic layer 1118 outputs the food identity 1130 and its confidence level 1132 to a data layer 1119 when the confidence level 1132 is above a threshold. The data layer 1119 constructs a frame list 1128 by combining all food identities 1130 and corresponding confidence levels 1132, and outputs the frame list 1128. Although not shown in FIG. 11, the nutritional information and volume may be stored with each food identity 1130 in the frame list 1128. Alternatively, the nutritional information and volume may be determined after the frame list 1128 is constructed.

In some embodiments, the frame 1102 is also inputted, without cropping, into the classifier 1112. When there is only one food item appearing in the frame 1102, the classifier 1112 can accurately identity the one food item from the uncropped frame 1102. In these embodiments, the classifier 1112 generates a second feature vector of classifier probabilities. A second predicted classifier class identifies the one food item in the uncropped frame 1102 with a top classifier probability that is higher than all other classifier probabilities in the second feature vector. The voting logic layer 1118 can then determine the food identity 1130 of the one food item, and a corresponding confidence level 1132, based on the predicted multiple-object class and probability, the top predicted classifier class and classifier probability for the cropped frame, and the top predicted classifier class and classifier probability for the uncropped frame. When the multiple-object detector 1111 returns more than one bounding box, the logic layer 1118 may ignore the second feature vector since the classifier 1112 is trained to classify only a single food, and therefore the classifier probabilities of the second feature vector are likely not high when there are multiple food items present in the frame 1102. However, the logic layer 1118 may still use the second feature vector even when there is more than one food item in the frame 1102.

Feeding OD and CL frames into the voting logic layer 1118, and potentially adding an additional frame as described above, are advantageous compared to prior-art methods (e.g., image augmentation techniques) because the present embodiments leverage a user's intent to recognize a food and log that food through small adjustments of the position of the mobile device. Whereas other methods, such as image-based recognition, rely exclusively on the performance of neural networks, the present embodiments give users the ability to augment neural-network performance by introducing a human-in-the-loop effect, which advantageously compensates for limitations of pure neural network-based approaches.

In some embodiments, the food-recognition engine 1100 includes a barcode detector 1114 that processes each frame 1102 to identify one or more barcodes appearing in the frame 1102 (see FIG. 8). For each found barcode, the barcode detector 1114 outputs an identifier number (e.g., a UPC code) to a database search module 1124 that searches a product database 1126 for the identifier number. If the identifier number is found, the database search module 1124 then retrieves a product name with the identifier number. The product name and a corresponding confidence level of 1 are passed to the data layer 1119, which outputs the product name and corresponding confidence as a food identity 1130 and confidence level 1132 in the frame list 1128.

In some embodiments, the multiple-object detector 1111 is pre-trained to recognize "bar code" as one of the multiple-object classes. When the multiple-object detector 1111 outputs "bar code" as the predicted multiple-object class, or when the multiple-object detector 1111 outputs a background class and the barcode detector 1114 returns a found barcode, the food-recognition engine 1100 assumes that the user is pointing the camera of the mobile device 103 towards a bar code, and wishes to log the associated product. In this case, the food-recognition engine 1100 ignores outputs from the multiple-object detector 1111, the classifier 1112, optical character recognition (see OCR engine 1115 below), and logo detection (see logo detector 1113 below), and operates only the barcode detector 1114 and database search module 1124 to find a matching product in the product database 1126. To improve accuracy, the barcode detector 1114 and database search module 1124 may combine the UPC codes detected from several sequential frames 1102 (e.g., 2, 3, 4, etc.) to increase the probability of obtaining the correct one, and to ensure that the user intends to log a food via a UPC code. While a greater number of sequential frames 1102 increases the probability of obtaining the correct UPC code, it also takes more time. In embodiments where the video stream is captured at 3 fps, the number of sequential frames 1102 may be set equal to three. During the sequential frames, the multiple-object detector 1111, classifier 1112, barcode detector 1114, and logo detection (see logo detector 1113 below) need not be operated, advantageously saving computational resources.

At the end of the frame sequence, the database search module 1124 searches the product database 1126 for the UPC code, and retrieves the matching product name and/or nutritional information. This retrieved data is displayed (e.g., via an editor card 210 on the touchscreen 109, as shown in FIG. 2). The user may modify the name, volume, and nutritional information, and may either log the result (e.g., by swiping the touchscreen 109, as shown in FIG. 1, or pressing a "Log" button in the editor card 210) or reject it. The food-recognition engine 1100 then returns to operating with the multiple-object detector 1111, classifier 1112, barcode detector 1114, and logo detection.

In some embodiments, the food-recognition engine 1100 includes an OCR engine 1115 that processes each frame 1102 to recognize text. The OCR engine 1115 may determine one or more identifier numbers appearing in the recognized text, such as a UPC code (e.g., UPC-A) appearing next to a corresponding barcode. Similar to the operation described above for the barcode detector 1114, the database search module 1124 may search the product database 1126 to find each identifier number, from which it determines a product name that is passed to the data layer 1119 for inclusion in the frame list 1128 as a food identity 1130.

In another example of text-based food recognition, the output of the OCR engine 1115 is inputted to a natural-language processing (NLP) module 1122 that looks for descriptive words in the recognized text, or converts the words into a vector to support searching in a vectorized language representation space. The NLP module 1122 may use term frequency-inverse document frequency (TFIDF) techniques, a recurrent neural network, or another type of machine-learning algorithm. The database search module 1124 then searches the product database 1126 to identify products containing one or more of the descriptive words, or those products that closely match a vector representation identified by the NLP module 1122. For example, the database search module 1124 may try to match the descriptive words to keywords stored with each identifier number in the product database 1126. These keywords may be stored as a separate description of the food item represented by each identifier number, or may be included in the food name itself. In any case, the database search module 1124 returns a most-likely product name that is passed to the data layer 1119 for inclusion in the frame list 1128 as a food identity 1130. The database search module 1124 may also return with a confidence level 1132 generated by the NLP module 1122 when it attempts to match the string generated by OCR engine to a string corresponding to a branded product stored in the product database 1126.

In another example of text-based food recognition, the output of the OCR engine 1115 is searched for the words "Nutrition Label", "Nutrition Facts", or other words or structured information indicating nutritional information printed on packaging. If these words are found, the food-recognition engine 1100 assumes that the user is pointing a camera of the mobile device 103 towards a nutrition label, and wishes to log the associated product (e.g., see FIG. 6). In this case, the food-recognition engine 1100 may ignore the outputs from the multiple-object detector 1111, classifier 1112, barcode detector 1114, and logo detection (see logo detector 1113 below). The food-recognition engine 1100 executes a Nutrition-Label logging module 1140 that uses the OCR-recognized text to produce a record of the nutritional information printed in the nutrition label (e.g., calories, serving size, carbs, fats, etc.). The Nutritional-Label logging module 1140 may be executed either in parallel with, or instead of, the NLP module 1122. Notably, once users log foods using Nutrition-Label logging, no further user action is required because a nutrition label generally contains all the information required to log a food item. The user may then log the food item, and either complete the logging process or go back to the general recognition flow.

Since OCR is statistical in nature, a single frame 1102 containing an identified nutrition label may result in imperfect determination of the nutritional information. Therefore, it is beneficial to use the results from multiple sequential frames 1102, especially since movement of the camera (e.g., due to an unsteady hand holding the mobile device 103) may impact OCR accuracy. For example, the amount of carbs may be missed in a first frame 1102, but would be captured in a subsequent second frame 1102. In another example, the first frame 1102 returns "10 calories" while second and third subsequent frames 1102 return "100 calories". In this case, it is more likely that "100 calories" is correct. The food-recognition engine 1100 selects the most consistent result out of three sequential frames 1102, but can be alternatively adjusted to select the most consistent result from a different number of sequential frames 1102 (e.g., 2, 3, 4, etc.). While a greater number of sequential frames 1102 increases the probability of obtaining the correct data, it also takes more time. In embodiments where the video stream is captured at 3 fps, the number of sequential frames 1102 may be set equal to three. During the sequential frames, the multiple-object detector 1111, classifier 1112, barcode detector 1114, and logo detection (see logo detector 1113 below) need not be operated, advantageously saving computational resources.

At the end of the sequence, the nutritional information may be displayed (e.g., on the touchscreen 109). The user may then add a name, add a volume, and modify the nutritional information (e.g., via an editor card 210 on the touchscreen 109, as shown in FIG. 2) The user may then either log the named food (e.g., by swiping the touchscreen 109) or reject it. The named food may then be passed to the data layer 1119 for inclusion in the frame list 1128 as a food identity 1130. The food-recognition engine 1100 then returns to operating with the multiple-object detector 1111, classifier 1112, barcode detector 1114, and logo detection.

In some embodiments, the food-recognition engine 1100 includes a logo detector 1113 that processes each frame 1102 to find one or more logos. Each found logo is inputted to a logo classifier 1116 to identify the logo. The logo classifier 1116 may be, for example, a convolutional neural network pre-trained to recognize a plurality of logos and output a feature vector of probabilities corresponding to the logos. A brand name associated with the logo having the highest probability is then passed to the database search module 1124, which searches the product database 1126 to return a list of products having the same brand name. Thus, each entry in the product database 1126 stores a brand name along with a product name, description, nutritional information, and other identifying information. Although not shown in FIG. 11, the product list is presented to the user (e.g., via a tray displayed on the touchscreen 109 of the mobile device 103), who may select one of the products, and additionally modify the name, volume, and nutritional information associated with the selected product (e.g., see FIG. 2). The user may then log the selected product (e.g., by swiping the touchscreen 109) or reject it. The selected product is passed to the data layer 1119 for inclusion in the frame list 1128 as a food identity 1130.

In some embodiments, the frame 1102 is sliced into a plurality of sliced images. For example, when the frame 1102 has a size of 4032×3024 pixels, it may be partitioned into 10×10=100 sliced images, each with a size of 403×302 pixels. Each of the sliced images is then processed by the food-recognition engine 1100, as described above. This slicing of the frame 1102 may improve classification accuracy when there are many different types of food present in the frame 1102 (e.g., an image of a refrigerator).

Voting Logic

Figure 14:
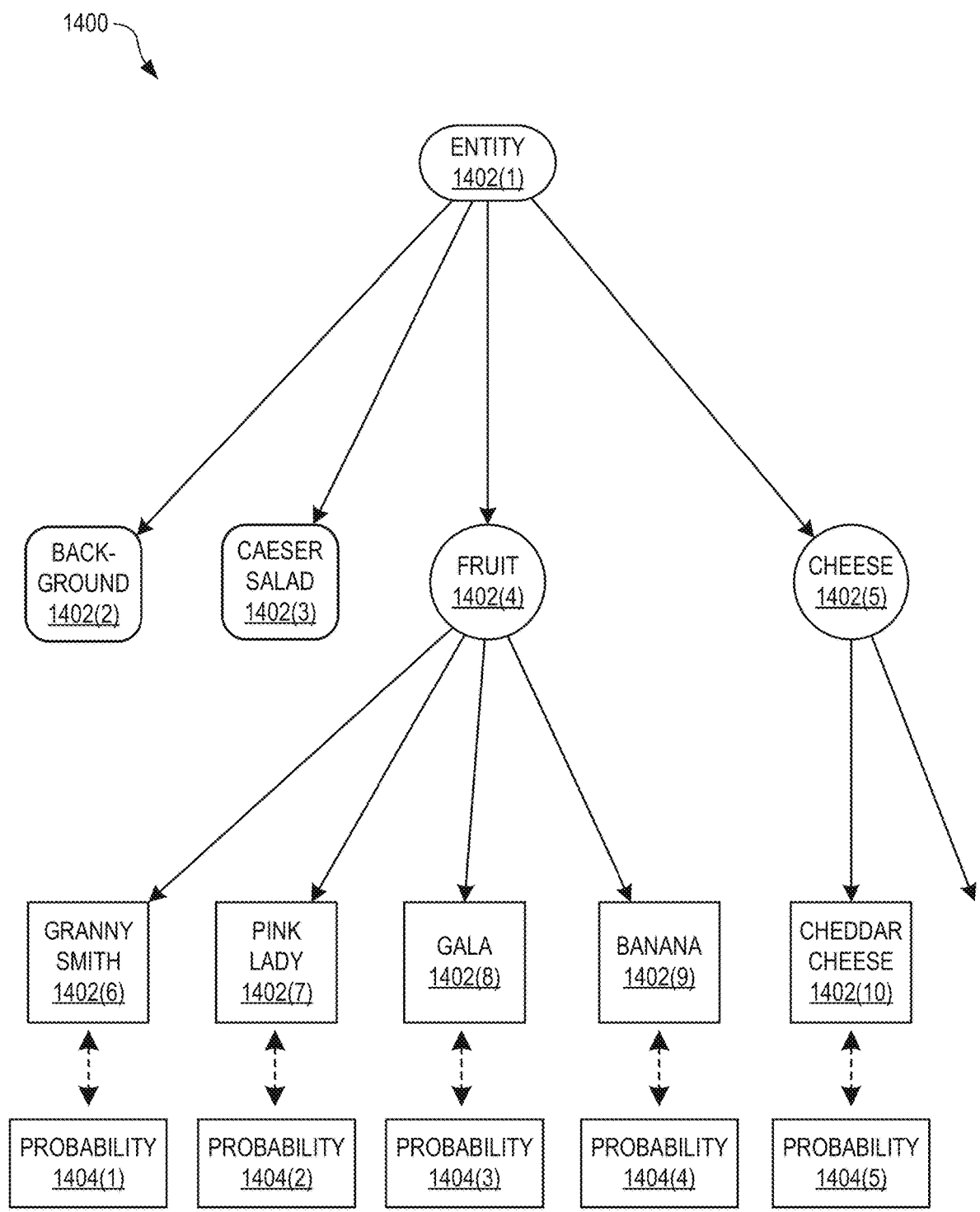
FIG. 14 shows a food hierarchy that the voting logic layer may use to predict a food identity, in an embodiment.

FIG. 14 shows a food hierarchy 1400 that, in some embodiments, the voting logic layer 1118 uses to predict a food identity 1130. The hierarchy 1400 is a tree-based data structure that is shown in FIG. 14 having leaf nodes 1402 shaped as squares (both rounded and unrounded), and internal nodes 1402 shaped as circles. Each node 1402 includes a label corresponding to a class (i.e., a food category or type). For clarity in the following discussion, only ten nodes 1402 of the food hierarchy 1400 are shown in FIG. 14. These ten nodes 1402 are organized into three levels, the first of which contains only a root node 1402(1) titled "Entity". In its entirety, the food hierarchy 1400 may have tens of thousands of nodes 1402, or more.

In embodiments, the multiple-object detector 1111 is trained to recognize a plurality of multiple-object classes that generally correspond to food "categories", whereas the classifier 1112 is trained to recognize a plurality of classifier classes that generally correspond to specific food items falling within the food categories. In the example of FIG. 14, the multiple-object detector 1111 is trained to recognize the food categories "Caesar Salad", "Fruit", and "Cheese", while the classifier 1112 is trained to recognize the specific food items "Granny Smith", "Pink Lady", "Gala", "Banana", "Cheddar Cheese", and "Caesar Salad". The multiple-object detector 1111 may also output "Background" to indicate that an image does not contain any of the food categories used for training the multi-object detector 1111. Similarly, the classifier 1112 may output "Background" to indicate that an image does not contain any of the specific food items used for training the classifier 1112. Although "Background" may be referred to herein as a multi-object class, classifier class, or both, it should be understood that the multiple-object detector 1111 and classifier 1112 are not trained to recognize "Background".

Each food category (i.e., multiple-object class) may encompass several specific food items (i.e., classifier classes). In the context of the hierarchy 1400, each specific food item is represented as one leaf node 1402 since the identity of a specific food item cannot be subdivided. In contrast, each food category may be represented as an internal node 1402 whose identity can be subdivided, in which case the internal node 1402 may have one or more leaf nodes 1402 as children (e.g., the leaf nodes 1402(6), 1402(7), 1402(8), and 1402(9) are children of the internal node 1402(4)). Alternatively, a food category may encompass only one food item that is the same as the food category. In this case, the food category is shown as a leaf node 1402 shaped as a rounded square (e.g., "Caesar Salad"), and represents a multiple-object class and a classifier class that are the same.

As an example of how the voting logic layer 1118 can use the hierarchy 1400 to improve the confidence levels of identified foods, consider a frame containing an image of a piece of fruit. The multiple-object detector 1111 may identify the image as "Cheese" with a multiple-object probability of 50%. The image may then be cropped using the bounding box returned by the multiple-object detector 1111, and processed by the classifier 1112 to obtain an array of classifier probabilities 1404 corresponding to specific food items. For example, the array may contain: "Pink Lady"=25%, "Granny Smith"=15%, "Gala"=10%, and "Banana"=8%. In FIG. 14, each classifier probability 1404 is connected to its corresponding specific food item via a dashed line. In this case, an implied probability that the image contains "Fruit" is 58% (i.e., the sum of the classifier probabilities 1404(1), 1404(2), 1404(3), and 1404(4)), which is higher than the multiple-object probability. Due to the higher probability, the voting logic layer 1118 identifies the food as "Fruit" instead of "Cheese".

Figure 15:
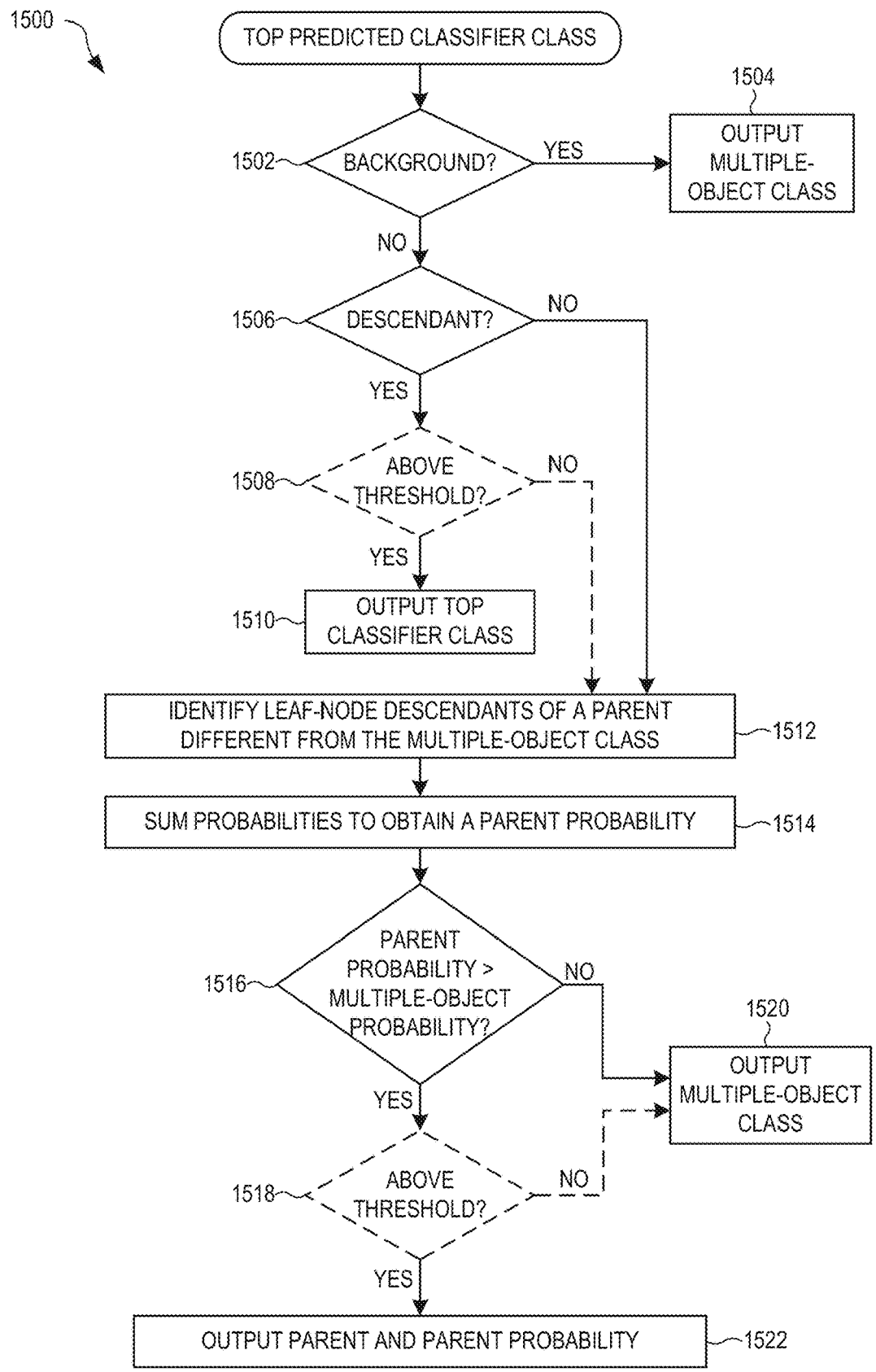
FIG. 15 is a block diagram of a method for determining a food identity from a video frame based on a hierarchical tree, in embodiments.

FIG. 15 is a block diagram of a method 1500 for determining a food identity from a video frame based on a hierarchical tree (e.g., the food hierarchy 1400 of FIG. 14). The method 1500 implements embodiments of the voting logic layer 1118 of FIG. 11, and may be repeated for each food item found by the multiple-object detector 1111 in a single video frame. The method 1500 is performed after (1) the multiple-object detector 1111 processes the video frame and returns a predicted multiple-object class (that is not background) and a corresponding multiple-object probability, and (2) the classifier 1112 processes the cropped video frame and returns an array of one or more classifier probabilities corresponding to one or more predicted classifier classes. This array may include classifier probabilities for all of the plurality of classifier classes. Alternatively, the array may exclude probabilities that are negligible (i.e., below a threshold). The one predicted classifier class with the largest classifier probability is referred to herein as the "top predicted classifier class".

In the decision block 1502 of the method 1500, the top predicted classifier class is checked to determine if the classifier 1112 identified the cropped video frame as background. If so, then the method 1500 continues to the block 1504, where the predicted multiple-object class is outputted as the food identity. As part of the block 1504, the multiple-object probability may be outputted as a confidence level of the food identity.

If the top predicted classifier class is not background, then the method 1500 continues to the decision block 1506, where the hierarchical tree is checked to determine if the top predicted classifier class is a child of the predicted multiple-object class. For example, the hierarchical tree may be checked to see if the node corresponding to the predicted classifier class is a leaf node that is a descendant of an internal node corresponding to the predicted multiple-object class. If so, then the method 1500 continues to the block 1510, where the top predicted classifier class is outputted as the food identity. As part of the block 1510, the largest classifier probability may be outputted as the confidence level of the food identity.

In some embodiments, the method 1500 includes the decision block 1508, where the largest classifier probability is compared to a first threshold. If the largest classifier probability exceeds the first threshold, then the method continues to the block 1510. If the largest classifier probability is below the first threshold, then the method continues to the block 1512.

If the top predicted classifier class is not a child of the predicted multiple-object class, then the method 1500 continues to the block 1512, where the parent of the top predicted classifier class (i.e., the internal node that is the parent of the leaf node corresponding to the top predicted classifier class) is identified. This parent will be different from the predicted multiple-object class. From the hierarchical tree, all leaf-node descendants of the parent (i.e., children nodes) are identified, one of which will be the top predicted classifier class. These identified leaf-node descendants are also referred to herein as sibling nodes since they all have the same parent node. The method then continues to the block 1514, where the classifier probabilities of these leaf-node descendants are summed to obtain a parent probability.

The method 1500 then continues to the decision block 1516, where the parent probability is compared to the multiple-object probability. If the parent probability is less than the multiple-object probability, then the method 1500 continues to the block 1520, where the predicted multiple-object class is outputted as the food identity. As part of the block 1520, the multiple-object probability may be outputted as the confidence level of the food identity.

In some embodiments, the method 1500 includes the decision block 1518, where the multiple-object probability is compared to a second threshold. If the multiple-object probability is below the second threshold, the method continues to the block 1520. If the multiple-object probability exceeds the second threshold, the method continues to the block 1522, where the parent (i.e., the food category corresponding to the parent node) is outputted as the food identity. As part of the block 1522, the parent probability may be outputted as the confidence level of the food identity.

The following computer code is an exemplary implementation of the method 1500. The following computer code implements the blocks 1508 and 1518 of the method 1500 using a value of 0.4 for each of the first and second thresholds.

```
def vote_logic(multi_object_class, multi_object_prob, top_classifier_class,
        top_classifier_prob, classifier_probabilities):
    if classifier_class == "Background":
        return multi_object_class, multi_object_prob
    #Classifier result is a descendant of multi_object, the two are aligned
```

```
if top_classifier_prob >= 0.4 and
    is_descendant_of(multi_object_class, top_classifier_class):
    return top_classifier_class, top_classifier_prob
#Classifier result is not a descendant of multi object
    #Check whether the probability of all siblings from the classifier result outweigh
    the multiple-object result
classifier_parent, classifier_siblings = find_sibling_indices(classifier_class)
classifier_parent_prob = 0.0
for sib in classifier siblings:
    classifier_parent_prob +=classifier_probabilities[sib]
if classifier_parent_prob > 0.4 and classifier_parent_prob > multi_object_prob:
    return classifier_parent, classifier_parent_prob
    else:
    return multi_object_class, multi_object_prob
```

To construct the food hierarchy 1400, the multiple-object and classifier classes are selected to form a one-to-many relationship such that each multiple-object class is a parent to several classifier classes, i.e., each food category contains, or encompasses, several specific food items. Whether a given "food" is a food category, a specific food item, or both, is a balance between three competing factors. First, it is advantageous to have a small number of classes, as this keeps the models (i.e., the multiple-object detector 1111 and classifier 1112) small, thereby minimizing computing resources and reducing the time needed to process the frames 1102. Second, a multiple-object class should correspond to visual features that are distinct enough to ensure that the multiple-object detector 1111 can accurately distinguish that class from other multiple-object classes. A multiple-object class whose visual features are too broad can degrade the accuracy of the multiple-object detector 1111. Third, a multiple-object class should correspond to visual features that are relatively close to those of the underlying, or encompassed, classifier classes, otherwise too many false positives may result for visually distinct foods within the multiple-object class. In some cases, the best approach is to include the food as both a multiple-object class and a classifier class (i.e., so that both the multiple-object detector 1111 and the classifier 1112 are trained with the same food).

The structure in which one multiple-object class is a parent to several classifier classes (e.g., see "Fruit" in FIG. 14) works well if the underlying children form a visual "cluster" with features that clearly distinguish the cluster from other visual clusters (each of these other visual clusters has its own parent node corresponding to a different multiple-object class). In this case, the path in the food hierarchy 1400 from the root node 1402(1) to each leaf node 1402 (corresponding to a classifier class) passes through exactly one internal node (corresponding to a multiple-object class).

Time Sequencing

Figure 16:
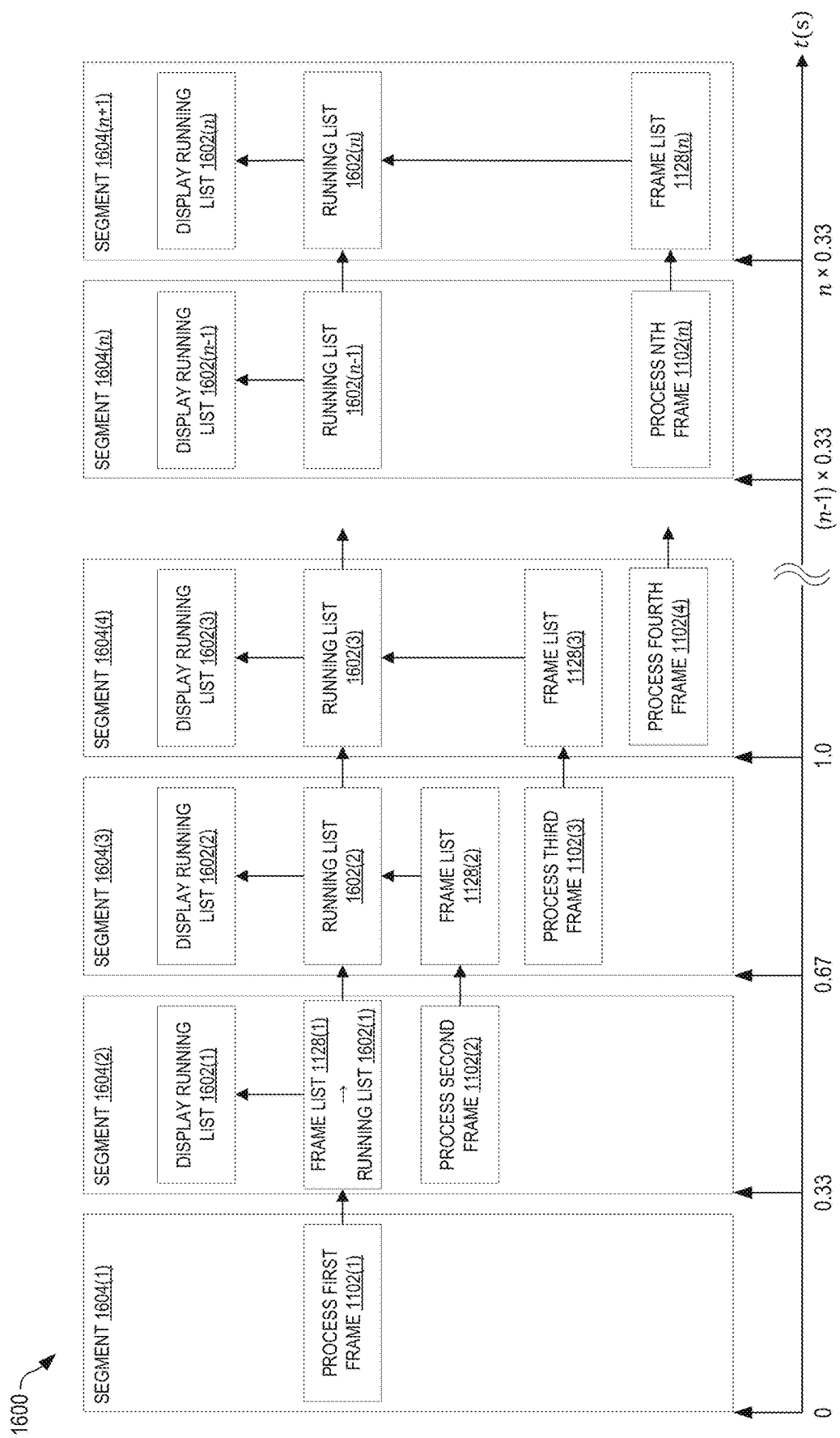
FIG. 16 illustrates a method for combining a frame list with a running list to generate an updated running list of identified foods, in embodiments.

FIG. 16 illustrates a method 1600 for combining each frame list 1128 with a running list 1602 to generate an updated running list 1602 of identified foods that are displayed to the user. Identifying foods across several consecutive frames, as exemplified by the method 1600, is referred to herein as "time sequencing". Advantageously, time sequencing can be used to improve the confidence level of an identified food. In FIG. 16, it is assumed that the video stream is obtained at a frame rate of 3 fps, and thus each frame 1102 is processed every $\Delta t=0.33$ s. However, $\Delta t$ may have any value (e.g., 100 ms corresponding to 10 fps, 17 ms corresponding to 60 fps, 1000 ms corresponding to 1 fps). In a first processing segment 1604(1) that starts at time $t=0$ s and ends at $t=\Delta t=0.33$ s, a first frame 1102(1) is processed to obtain a first frame list 1128(1). In a second processing segment 1604(2) that starts at $t=\Delta t=0.33$ s and ends at $t=2\Delta t=0.67$ s, the first frame list 1128(1) is stored as an initial running list 1602(1), the initial running list 1602(1) is displayed, and a second frame 1102(2) is processed to obtain a second frame list 1128(2). In a third processing segment 1604(3) that starts at $t=2\Delta t=0.67$ s and ends at $t=3\Delta t=1.0$ s, the second frame list 1128(1) and first running list 1602(1) are combined to create a second running list 1602(2) that is displayed. At the same time, a third frame 1102(3) is processed to obtain a third frame list 1128(3). In a fourth processing segment 1604(4) that starts at $t=3\Delta t=1.0$ s and ends at $t=4\Delta t=1.33$ s, the third frame list 1128(3) and second running list 1602(2) are combined to create a third running list 1602(3) that is displayed while a fourth frame 1102(4) is processed. This process continues in this manner, as shown, such that during an $(n+1)^{th}$ processing segment 1604($n$+1), a frame list 1128($n$) and a running list 1602($n$−1) are combined to create a running list 1602($n$) that is displayed.

To combine a frame list 1128($i$) and a running list 1602($i$−1) into an updated running list 1602($i$), a weighted sum of confidence levels may be computed for each food identity 1130 that appears in both the running list 1602($i$−1) and the frame list 1128($i$). Specifically, the weighted sum is calculated from the confidence level of the food identity 1130 stored in the running list 1602($i$−1) and the confidence level of the food identity 1130 stored in the frame list 1128($i$). If the weighted sum is above a threshold, then the food identity 1130 is added to the updated running list 1602($i$), and the weighted sum is added to the updated running list 1602($i$) as the corresponding food-identity confidence level 1132. If the weighted sum is below the threshold, the food identity 1130 is excluded from the updated running list 1602($i$).

For each food identity 1130 found in only one of the frame list 1128($i$) and the running list 1602($i$−1), it is assumed that the food identity 1130 has a confidence level of 0 for the list in which it does appear. In this case the weighted sum simplifies to a scaling of the one confidence level that is available. If the weighted sum is above the threshold, the food identity 1130 is added to the updated running list 1602($i$), and the weighted sum is added to the updated running list 1602($i$) as the corresponding food-identity confidence level 1132. If the weighted sum is below the threshold, the food identity 1130 is excluded from the updated running list 1602($i$).

The weights used to calculate the weighted sum may be selected to upweight the confidence levels stored in the frame list 1128($i$), which preferentially selects food identities in the frame list 1128($i$) for inclusion in the updated running list 1602($i$). Alternatively, the weights may be selected to downweight the confidence levels stored in the frame list 1128($i$), which preferentially selects food identities stored in the running list 1602(*i*−1) for inclusion in the updated running list 1602(*i*). Downweighting is equivalent to giving the running list 1602 a "long" memory, to increase the likelihood that a food identity already stored in the running list 1602 remains therein. Similarly, upweighting is equivalent to giving the running list 1602 a "short" memory, as it is less likely for a food identity already stored in the running list 1602 to remain therein (unless it also appears in the frame list 1128).

The sequence of running lists 1602 is a time series, and the example of confidence-level weighting described above is one example of a time-series model used for time-series forecasting. This example may be expanded to include other types of time-series models, such as moving-average models, autoregressive models, and others. Other methods of weighting and/or combining the frame list 1128(*i*) and the running list 1602(*i*−1) into the updated running list 1602(*i*) may be used without departing from the scope hereof. This includes using more than just the most-recent frame list 1128(*i*) to update the running list 1602(*i*−1). For example, the two most-recent frame lists 1128(*i*−2) and 1128(*i*−1) may be used to update the running list 1602(*i*−1). More generally, any n most-recent frame lists may be combined (via weighting) to update the running list 1602(*i*−1).

In some embodiments, downweighting and upweighting are determined in response to motion of the mobile device 103. Specifically, the weights used for weighting the confidence levels are based on a motion signal detected by the mobile device 103 (e.g., from an accelerometer). A motion signal with a relatively large magnitude likely indicates that the user has intentionally moved the mobile device 103 such that the camera is pointing at a new food item. In this case, it is more likely that previously detected food items stored in the running list 1602(*i*−1) are no longer valid and should be ignored. Accordingly, confidence levels from the running list 1602(*i*−1) are downweighted while confidence levels from the frame list 1128(*i*) are upweighted. Similarly, a motion signal with a relatively small magnitude likely indicates that the user is intentionally keeping the mobile device 103 still for a duration lasting several consecutive frames 1102. In this case, the running list 1602(*i*−1) may beneficially help with food identification. Accordingly, confidence levels from the running list 1602(*i*−1) may be upweighted while confidence levels from the frame list 1128(*i*) are downweighted.

As an example of how time sequencing can be used to track foods appearing in a sequence of frames 1102, consider a first frame 1102(1) with a first frame list 1128(1):

Frame_List[1]=(Orange, Apple, Banana, Apricot).

Each food identity 1130 is stored in Frame_List[1] without a corresponding confidence level 1132. For example, the data layer 1119 may have only added each food identity 1130 to Frame_List[1] when the corresponding confidence level 1132 exceeds a threshold. The first food identity 1130 in Frame_List[1] may then be added, or enqueued, to a "most-seen" queue of one or more elements that is initially empty. After enqueuing:

Most_Seen_Queue=(Orange).

The most-seen queue may then be processed to count the number of elements, or occurrences, of each food identity 1130 therein. In this case, the most-seen queue has only one element with the food identity "Orange". This one food identity may then be displayed to the user.

A second frame 1102(2) may have a second frame list 1128(2):

Frame_List[2]=(Apricot, Orange, Apple, Banana).

The first food identity 1130 in Frame_List[2] is then enqueued to the most-seen queue:

Most_Seen_Queue=(Orange, Apricot).

Counting the number of elements of each food identity in Most_Seen_Queue yields: {Orange: 1, Apricot: 1}. Here, "Orange" and "Apricot" were both seen the same number of times in the first two frames 1102(1), 1102(2). In this case, the most-recent food identity enqueued to Most_Seen_Queue (i.e., "Apricot") is displayed.

A third frame 1102(3) may have a third frame list 1128(3):

Frame_List[3]=(Orange, Apple, Banana).

The first food identity 1130 in Frame_List[3] is enqueued to the most-seen queue:

Most_Seen_Queue=(Orange, Apricot, Orange).

Counting the number of elements of each food identity in Most_Seen_Queue yields: {Orange: 2, Apricot: 1}. Here, "Orange" is the most-seen food identity 1130, and is therefore displayed.

A fourth frame 1102(4) may have a fourth frame list 1128(4):

Frame_List[4]=(Banana, Strawberry).

The first food identity 1130 in Frame_List[4] is enqueued to the most-seen queue:

Most_Seen_Queue=(Orange, Apricot, Orange, Banana).

Counting the number of elements of each food identity in Most_Seen_Queue yields: {Orange: 2, Apricot: 1, Banana: 1}. Again, "Orange" is the most-seen food identity 1130, and is therefore displayed.

A fifth frame 1102(5) may have a fifth frame list 1128(5):

Frame_List[5]=(Banana, Blueberry).

The first food identity 1130 in Frame_List[5] may be enqueued to the most-seen queue such that Most_Seen_Queue has five elements. However, an element in Most_Seen_Queue may first be dequeued if the size of Most_Seen_Queue equals a maximum number. For example, if the maximum number if four, then the first element of Most_Seen_Queue (i.e., "Orange") may first be dequeued before enqueuing the first food identity 1130 in Frame_List[5]. The result is:

Most_Seen_Queue=(Apricot, Orange, Banana, Banana).

Counting the number of elements of each food identity in Most_Seen_Queue yields: {Orange: 1, Apricot: 1, Banana: 2}. Now, "Banana" is the most-seen food identity 1130, and is therefore displayed.

In the above example, there are several variations that can be implemented. For example, more than one food identity 1130 in each frame list 1128 can be enqueued to the most-seen queue. More than one most-seen food identity 1130 in the most-seen queue can be displayed. And more than one element can be dequeued from the most-seen queue (to ensure that the size of the most-seen queue doesn't exceed the maximum number).

Figure 17:
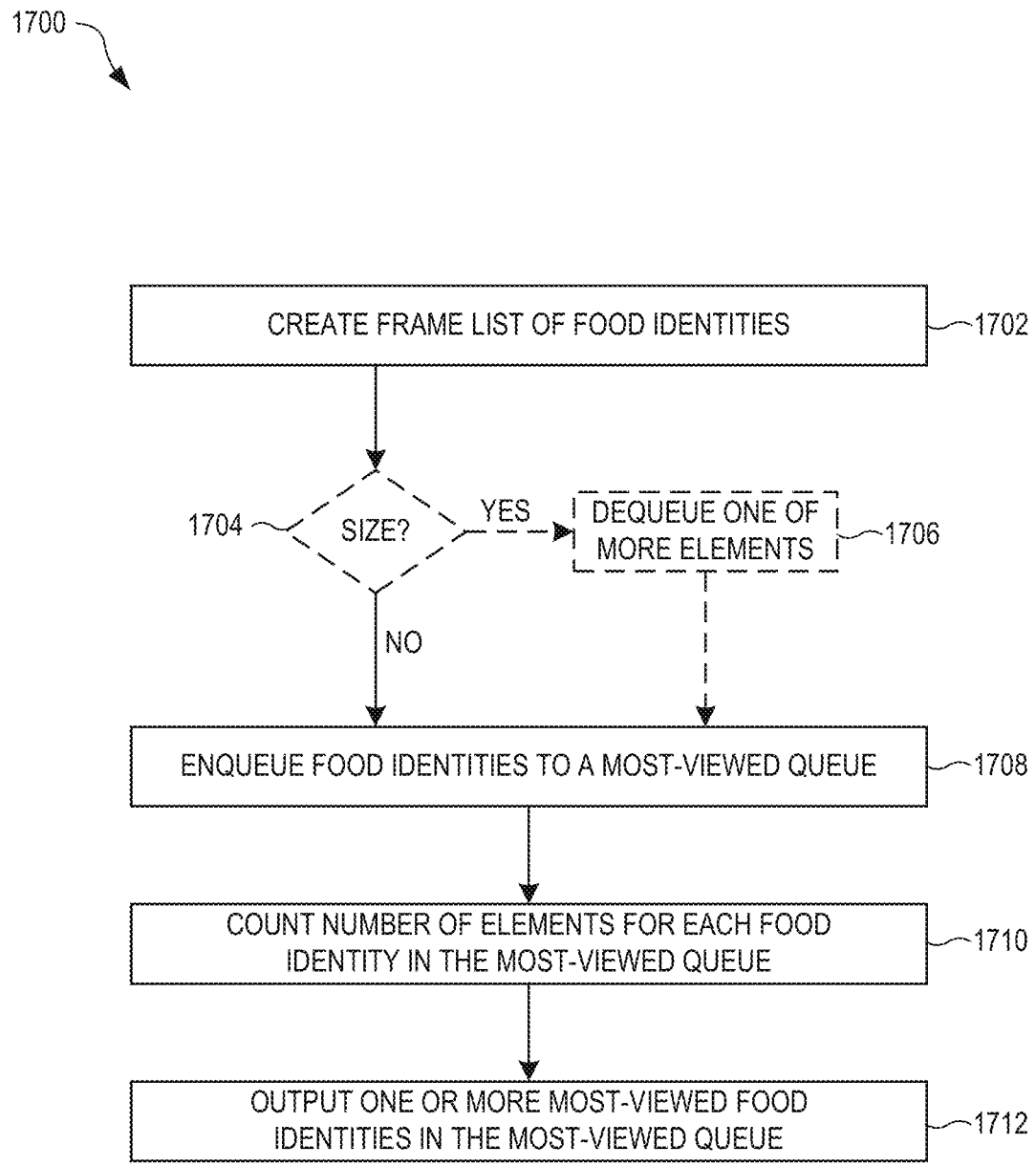
FIG. 17 is a flow chart of a method for identifying most-seen foods in a sequence of video frames, in an embodiment.

FIG. 17 is a flow chart of a method 1700 for identifying most-seen foods in a sequence of video frames. The method 1700 repeats for each frame 1102 in a sequence of consecutive frames 1102. Each iteration of the method 1700 includes the blocks 1702, 1708, 1710, and 1712. In some embodiments, each iteration also includes blocks the 1704 and 1706.

In the block 1702, a frame list of one of more food identities is created for a frame 1102(*i*). In one example of the block 1702, the food-recognition engine 1100 of FIG. 11 outputs the frame list 1128 containing one or more food identities 1130.

In some embodiments, the method 1700 continues to the block 1704 after the block 1702. In the block 1702, the size of a most-viewed queue is compared to a maximum size. If the size (i.e., number of elements) of the most-viewed queue is greater than or equal to the maximum size, then the method 1700 continues to the block 1706, where one or more elements of the most-viewed queue are dequeued.

If the size of the most-viewed queue is less than the maximum size, then the method 1700 continues to the block 1708, where one or more food identities in the frame list are enqueued to the most-viewed queue. The method 1700 then continues to the block 1710, where, for each food identity in the most-viewed queue, the number of elements storing said each food identity are counted. These counts may then be ranked to determine one or more most-viewed food identities.

The method 1700 then continues to the block 1712, where the one or more most-viewed food identities are outputted. In one example of the block 1712, the one or more most-viewed food identities are added to a running list 802 for display to a user (e.g., on the touchscreen 109 of the mobile device 103).

The following computer code is an exemplary implementation of the method 1700 for the case where only one most-viewed food identity is outputted. In the following computer code, the term "passioID" corresponds to a food identity in the previous discussion.

in this example, the two food identities in Frame_List[2] (i.e., "Apple" and "Peach") already appear in Running_List. In this case, the probability for a food identity stored in Running_List can be updated based on the corresponding probability stored in Frame_List[2]. For example, the probability of "Apple" stored in Running_List may be calculated as an average of the existing probability stored in Running_List (i.e., 0.9) and the new probability in Frame_List[2] (i.e., 0.98). The probability of "Peach" may be updated similarly, leading to:

Running_List={(Apple, 0.94), (Peach, 0.53)}.

More generally, the updated probability stored in Running_List may be calculated as a weighted sum of the previous probability stored in Running_List and the new probability from the most recent frame list 1128. Other methods of updating the probability may be used without departing from the scope hereof.

One or more food identities in the running list may be outputted (e.g., displayed on the screen of a mobile device) starting with a third frame 1102(3). For example, any food identity in Running_List, after the second frame 1102(2), whose probability exceeds a threshold (e.g., 0.6) may be outputted. In this example, only "Apple" would be displayed on the screen of the mobile device. The corresponding probability (i.e., 0.94) may also be displayed. Alternatively, a fixed number of highest-ranked (based on probability) food identities in Running_List may be outputted.

```
private func findMostSeen(compoundCandidates: [CompoundCandidate] )-> PassioID? {
    guard let passioID = compoundCandidates.first?.NotedCandidate.passioID else {
        mostSeenPassioID = []
        return nil
    }
    mostSeenPassioID.append(passioID)
    if mostSeenPassioID.count == 1 {//first one
        return passioID
    }else if mostSeenPassioID.count > passioSDK.mostSeenNumberOfFrames {
        mostSeenPassioID.removeFirst()
    }
    let mappedPassioID = mostSeenPassioID.map { ($0, 1) }
    let counts = Dictionary(mappedPassioID, uniquingKeysWith: +)
    let sorted = counts.sorted { $0.1 > $1.1 }
    if let mostPID = sorted.first, mostPID.value >1 {
        return mostPID.key
    } else {
        return passioID
    }
}
```

In some embodiments, time sequencing is implemented by including probabilities in the frame lists. These probabilities can be used to determine which food identities are displayed. For example, consider a first frame 1102(1) with a first frame list:

Frame_List[1]={(Apple, 0.9), (Peach, 0.86)}

Here, each entry in Frame_List[1] is a 2-tuple that combines a food identity with the probability determined by the voting logic layer 1118. Any food identity in Frame_List[1] may then be inserted to a running list (e.g., see the running list 1602 in FIG. 16) that is initially empty. The food identity may be inserted with its corresponding probability (i.e., the entire 2-tuple may be inserted). For the first frame 1102(1), this gives:

Running_List={(Apple, 0.9), (Peach, 0.86)}.

Here, Running_List is simply equal to Frame_List(1).

A second frame 1102(2) may have a second frame list 1128(2):

Frame_List[2]={(Apple, 0.98), (Peach, 0.2)}.

Any food identity in Frame_List[2] that is not already present in Running_List may be inserted thereto. However, The third frame 1102(3) may have a second frame list 1128(3):

Frame_List[3]={(Apple, 0.94), (Mango, 0.1)}.

Here, "Apple" already appears in Running_List, and therefore may be updated as described above. Mango does not appear in Running_List, and therefore may be inserted to Running_List with the average of its current frame-list probability (i.e., 0.1) and its previous running-list probability (i.e., 0 since it did not appear in Running_List). Similarly, "Peach" may be updated based on its current probability (i.e., 0 since it did not appear in the frame-list) and its previous running-list probability (i.e., 0.85). This gives:

Running_List={(Apple, 0.94), (Peach, 0.265), (Mango, 0.05)}.

For a fourth frame 1102(4), only "Apple" would be displayed since this is the only identity in Running_List whose probability exceeds the threshold.

When a food identity is absent for several consecutive frames 1102, its probability in the running list will continue to decrease. The rate at which it decreases will depend on the weighting. At a certain frame, the probability may be so low that the food identity may be removed from the running list.

Figure 18:
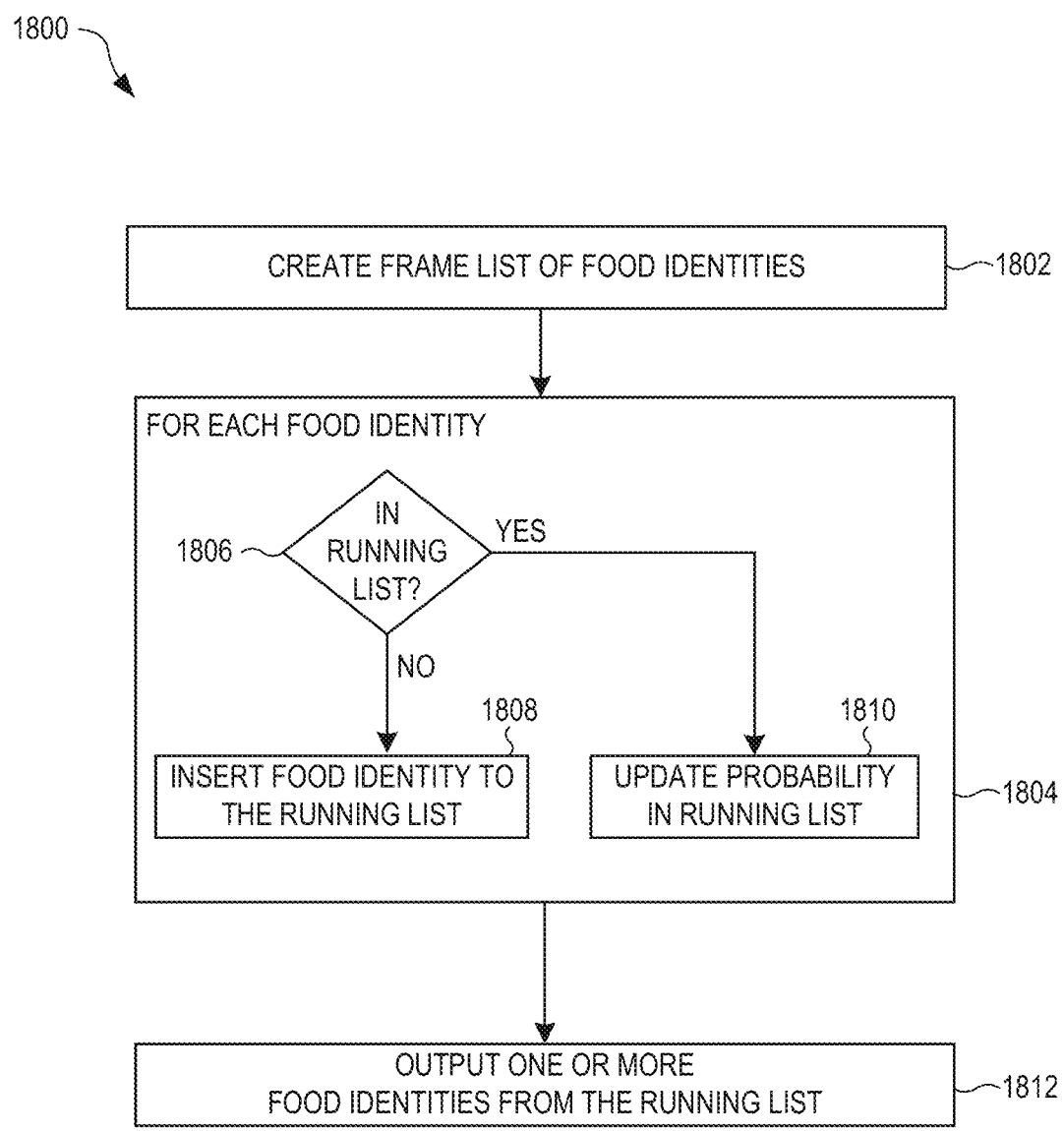
FIG. 18 is a flow chart of another method for identifying most-seen foods in a sequence of video frames, in an embodiment.

FIG. 18 is a flow chart of a method 1800 for identifying most-seen foods in a sequence of video frames. The method 1800 repeats for each of a sequence of consecutive frames 1102. Each iteration of the method 1800 includes the blocks 1802, 1804, and 1812. In the block 1802, a frame list of one or more food identities is created for a frame 1102(i). In one example of the block 1802, the food-recognition engine 1100 of FIG. 11 outputs the frame list 1128 containing one or more food identities 1130 and corresponding one or more confidence levels 1132.

The block 1804 repeats for each food identity in the frame list. In the decision block 1806, a running list is searched for the food identity. If the food identity is found, the method 1800 continues to the block 1810, where the probability of the food identity stored in the running list is updated. In one example of the block 1810, a weighted sum is calculated from the existing probability in the running list and the new probability from the frame list. This weighted sum then replaces the existing probability in the running list.

If the food identity is not found, the method 1800 continues to the block 1808, where the food identity, and a corresponding probability, are inserted into the running list. In one example of the block 1808, a weighted sum is calculated from 0 (i.e., the existing probability of the food identity in the running list) and the new probability from the frame list. This weighted sum is the corresponding probability stored in the running list.

The method 1800 then continues to the block 1812, where one or more food identities in the running list are outputted. In one example of the block 1812, all food identities in the running list with a probability over a threshold are outputted for display on a mobile device (e.g., see FIGS. 1-5).

KNN Predictor

Figure 19:
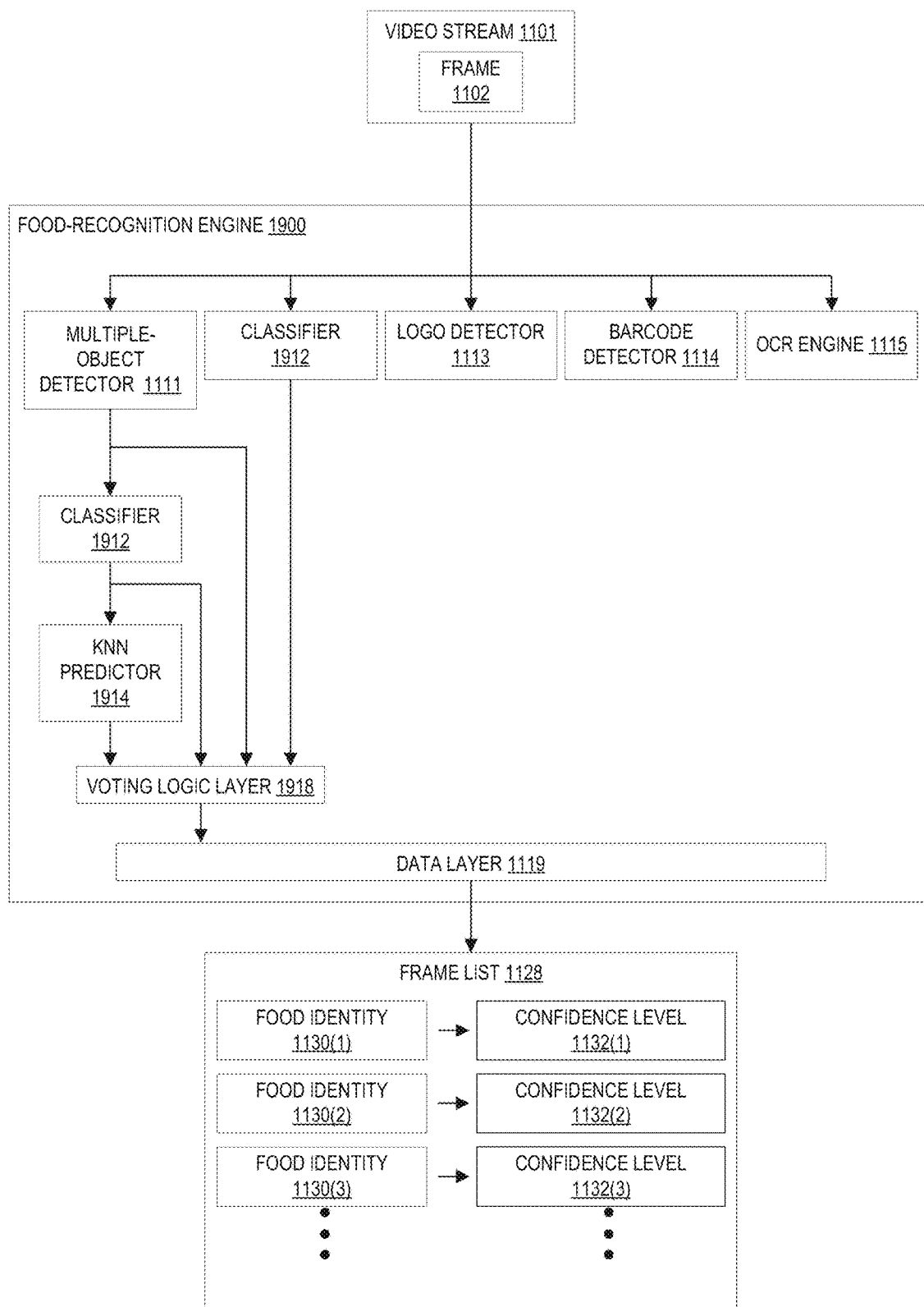
FIG. 19 is a block diagram of a food-recognition engine that is similar to the food-recognition engine of FIG. 11, except that it additionally uses a kth-nearest-neighbor predictor to improve accuracy, in embodiments.

FIG. 19 is a block diagram of a food-recognition engine 1900 that is similar to the food-recognition engine 1100 of FIG. 11, except that it uses a kth-nearest-neighbor (KNN) predictor 1914 to improve the accuracy of the food identities 1130. The voting logic layer 1918 is the similar to the voting logic layer 1118 of FIG. 11 in that it generates the best prediction for a food identity 1130. However, the voting logic layer 1118 additionally uses the output of the KNN predictor 1914. For clarity, some of the components of the food-recognition engine 1900 are not shown in FIG. 19.

The classifier 1912 is similar to the classifier 1112 of FIG. 11 in that it returns a feature vector storing one or more classifier probabilities corresponding to one or more predicted classifier classes of the plurality of classifier classes. The predicted classifier class with the highest classifier probability is also referred to herein as the top predicted classifier class. However, the classifier 1912 also returns a predicted vector that identifies the location of the top predicted classifier class in a vector space of class embeddings. The predicted vector is typically extracted from the penultimate layer of the classifier 1912 and has a norm of 1. The predicted vector is then passed to the KNN predictor 1914, as shown in FIG. 19.

The KNN predictor 1914 compares the predicted vector to the known class embeddings in the vector space. Here, the class embeddings are "known" in that they were pre-generated based on the classes of the leaf nodes 1402 of the tree-based food hierarchy 1400. Each of these leaf-node classes has an embedding vector in the vector space whose location is based on semantic similarity, as opposed to visual similarity. Specifically, two embedding vectors are "close" to each other in the vector space if the corresponding classes are semantically similar (e.g., "Granny Smith" and "Gala" in FIG. 14). Similarly, two embedding vectors are "far" from each other if the corresponding classes are semantically dissimilar (e.g., "Caesar Salad" and "Cheddar Cheese" in FIG. 14). Here, "far" and "close" are quantified by a distance metric of the vector space, such as a Euclidean or Manhattan distance. More details about class embedding can be found in "Hierarchy-based Image Embeddings for Semantic Image Retrieval" by Björn Barz and Joachim Denzler (2019 IEEE Winter Conference on Applications of Computer Vision (WACV), 2019 IEEE Winter Conference on Applications of Computer Vision (WACV), Waikoloa Village, HI, USA, 2019, pp. 638-647, doi: 10.1109/WACV.2019.00073).

The KNN predictor 1914 uses k-nearest neighbor classification (with k=1) to identify, in the vector space, the embedding vector that is closest to the predicted vector received from the classifier 1912. The class associated with this closest embedding vector is referred to herein as the "closest class". Most of the time, the closest class is the same as the top predicted classifier class. In this case, the KNN predictor 1914 has confirmed that the top predicted classifier class appears in the image, further improving the accuracy of the resulting food identity 1130.

However, in some cases, the closest class is different from the top predicted classifier class. In this case, the different results from the KNN predictor 1914 and classifier 1912 may indicate that any food in the processed image may not be easily identifiable. These different results may then be used, for example, to discard both the top predicted classifier class and the closest class. Therefore, the KNN predictor 1914 checks the output of the classifier 1912, advantageously reducing the number of food identities 1130 that are false positives.

One reason why the classifier 1912 and KNN predictor 1914 may have different outputs (i.e., the top predicted classifier class and the closest class are different) is that the classifier 1912 and KNN predictor 1914 are trained using different loss functions. For example, the classifier 1912 may be trained using cross-entropy, while the KNN predictor 1914 may use the loss function shown in Eqn. 8 in the above reference by Barz and Denzler.

The following computer code shows one example of how the voting logic layer 1918 uses the output of the KNN predictor 1914 to determine a food identity 1130. In the following computer code, the term "OD" represents the predicted multiple-object class returned by the multiple-object detector 1111, "CL" represents the top predicted classifier class returned by the classifier 1912, and "KNN" represents the closest class returned by the KNN predictor 1914. Furthermore, "isDescendant(A, B)" is true if, in the food hierarchy 1400, the node 1402 for B is a child of the node 1402 for A. For example, isDescendant("Fruit", "Gala")=True, while isDescendant("Caesar Salad", "Granny Smith")=False. Furthermore, "isSibling(A, B)" is true if, in the food hierarchy 1400, the node 1402 for B is a sibling of the node 1402 for A. For example, isSibling("Gala", "Banana")=True, while isSibling("Pink Lady", "Cheddar Cheese")=False.

```
Def filterNoneRelative(OD, CL, KNN):
    If isDescendant(OD, CL) or OD == CL or isSibling(OD, CL)
        and (isSibling(CL, KNN) or KNN == CL):
        Return CL
    Else
        Return background
```

This computer code checks if CL is either the same as OD, a descendant of OD, or a sibling of OD. If not, then CL and OD are different enough to prevent an accurate determination of the food identity 1130. In this case, "background" is returned. If true, the computer code also checks if KNN is either the same as CL or a sibling of CL. If so, KNN and CL are close enough in identity that CL is outputted as the food identity 1130. However, if KNN and CL are both different and not siblings, then KNN and CL are different enough to prevent an accurate determination of the food identity 1130. In this case, "background" is returned.

The following computer code shows another example of the voting logic layer 1918. In this example, the computer checks if KNN is either the same as CL or a sibling of CL. If so, KNN and CL are close enough in identity that CL is outputted as the food identity 1130. If not, "background" is returned. Note that this example does not use OD.

```
Def lessStrict(CL, KNN):
    If (isSibling(CL, KNN) or KNN == CL):
        Return CL
    Else:
        Return background
```

These two examples differ in how "strict" the classes must agree in order to determine food identity 1130. The voting logic layer 1918 may implement other methods of using the closet class to assist in determining a food identity 1130 without departing from the scope hereof. In some embodiments, the voting logic layer 1918 may implement multiple methods for determining a food identity 1130 (e.g., with various levels of strictness), wherein a user can select between methods to change the outputted results. In this way, the user can try different methods to see which produces food identities 1130 that are most accurate.

System Embodiments

Figure 20:
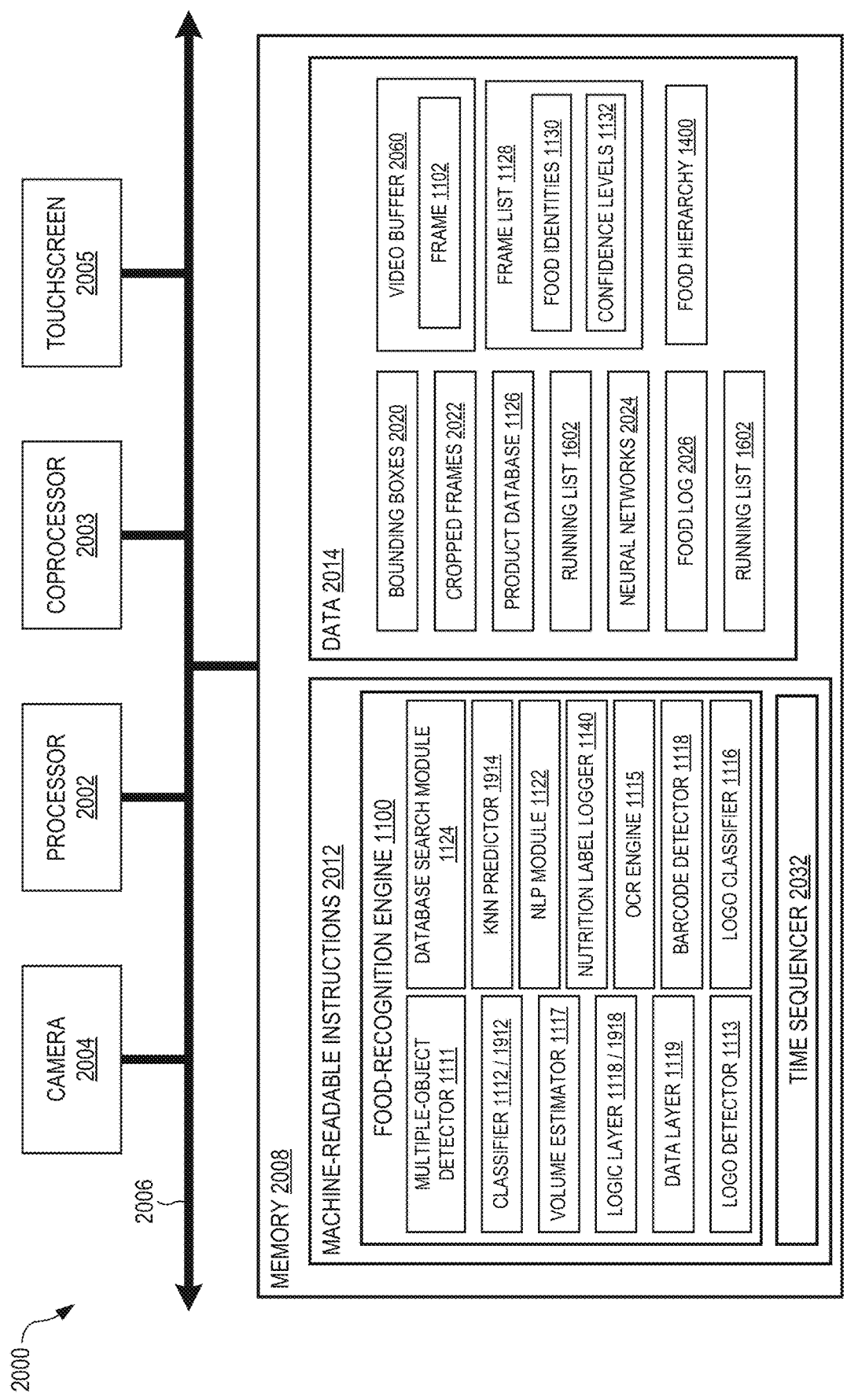
FIG. 20 is a functional diagram of a food-recognition system, in embodiments.

FIG. 20 is a functional diagram of a food-recognition system 2000 that implements the methods and functionality described above. The food-recognition system 2000 is a computing device having a processor 2002 and a memory 2008 that communicate over a system bus 2006. In embodiments, the food-recognition system 2000 further includes one or both of a camera 2004 and a touchscreen 2005 that are also communicably coupled to the system bus 2006. The mobile device 103 of FIGS. 1-10 is one example of the food-recognition system 2000, or a computing system that includes the food-recognition system 2000.

The processor 2002 may be any type of circuit capable of performing logic, control, and input/output operations. For example, the processor 2002 may include one or more of a microprocessor with one or more central processing unit (CPU) cores, a graphics processing unit (GPU), a digital signal processor (DSP), a field-programmable gate array (FPGA), a system-on-chip (SoC), and a microcontroller unit (MCU). The processor 2002 may also include a memory controller, bus controller, and other components that manage data flow between the processor 2002, camera 2004, touchscreen 2005, and memory 2008. In some embodiments, the food-recognition system 2000 includes a co-processor 2003 (e.g., a GPU, FPGA, or machine-learning accelerator) that is communicably coupled with the processor 2002 over the system bus 2006.

The memory 2008 stores machine-readable instructions 2012 that, when executed by the processor 2002 (and the co-processor 2003, when present), control the food-recognition system 2000 to implement the functionality and methods described above. Specifically, the food-recognition engine 1100 of FIG. 11 is shown in FIG. 20 as being stored in the memory 2008 as machine-readable instructions 2012. The memory 2008 also stores data 2014 used by the processor 2002 (and the co-processor 2003, when present) when executing the machine-readable instructions 2012, such as bounding boxes 2020 returned by the multiple-object detector 1111, cropped frames 2022 generated when cropping the frame 1102 according to the bounding boxes 2020, and a video buffer 2060 that stores one or more frames 1102 of a video stream generated by the camera 2004. The memory 2008 also stores neural networks 2024, which includes weights, biases, and other configuration data for the CNNs (and other machine-learning models, when implemented) used by one or more of the multiple-object detector 1111, classifier 1112, logo detector 1113, logo classifier 1116, barcode detector 1114, NLP module 1122, classifier 1912, and KNN predictor 1914. The memory 2008 may store additional machine-readable instructions 2012 than shown in FIG. 20 without departing from the scope hereof. Similarly, the memory 2008 may store additional data 2014 than shown in FIG. 20 without departing from the scope hereof.

In some embodiments, the food-recognition system 2000 includes additional machine-readable instructions 2012 to output a food identity (e.g., one of the food identities 1130). For example, the food-recognition system 2000 may display the food identity on the touchscreen 2005 (e.g., see FIGS. 1-5 and 9-10). The food-recognition system 2000 may also display the video stream on the touchscreen 2005. In some embodiments, the food-recognition system 2000 outputs the food identity by transmitting it to another computing device (e.g., wirelessly over Wi-Fi, or wired over Ethernet). The food-recognition system 2000 may similarly transmit the video stream to the other computing device.

In some embodiments, the food-recognition system 2000 includes machine-readable instructions 2012 to capture the video stream from the camera 2004 and store the video stream in the video buffer 2060. The video stream may be captured at a frame rate greater than or equal to one frame-per-second. In other embodiments, the food-recognition system 2000 excludes the camera 2004, in which case the video stream may be transmitted to the food-recognition system 2000 for storage and processing. The food-recognition system 2000 may also display the video stream on the touchscreen 2005 as it is acquired from the camera 2004.

In some embodiments, the food-recognition system 2000 stores a time sequencer 2032 that implements one or more of the methods 1600, 1700, and 1800. The time sequencer 2032 includes machine-readable instructions 2012 stored in the memory 2008. When executed by the processor 2002 (and co-processor 2003, when present), the time sequencer 2032 controls the food-recognition system 2000 to process each frame 1102 to update the running list 1602. The time sequencer 2032 may call the food-recognition 1100 for each frame 1102 to obtain the corresponding frame list 1128. The time sequencer 2032 may also use a most-viewed queue or most-viewed list (not shown in FIG. 20) to determine which food identities to output.

Changes may be made in the above methods and systems without departing from the scope hereof. It should thus be noted that the matter contained in the above description or shown in the accompanying drawings should be interpreted as illustrative and not in a limiting sense. The following claims are intended to cover all generic and specific features described herein, as well as all statements of the scope of the present method and system, which, as a matter of language, might be said to fall therebetween.

What is claimed is:

1. A food-recognition method, comprising:
inputting each frame, of a plurality of frames of a video stream, into a multiple-object detector to obtain (i) a bounding box identifying where each food item, of one or more food items, appears within said each frame, and (ii) a predicted multiple-object class identifying said each food item with a multiple-object probability;
for each bounding box:
cropping said each frame into a cropped frame based on said each bounding box;
inputting the cropped frame into a classifier to obtain one or more predicted classifier classes that identify said each food item with corresponding one or more classifier probabilities; and
determining a food identity of said each food item based on the predicted multiple-object class, the multiple-object probability, the one or more predicted classifier classes, and the corresponding one or more classifier probabilities;
creating a frame list of the one or more food identities determined from said each frame;
enqueuing at least one of the one or more food identities in the frame list into a most-viewed queue of elements to create an updated most-viewed queue; and
outputting at least one of the one or more food identities in the updated most-viewed queue.

2. The food-recognition method of claim 1,
further comprising displaying the video stream on a screen of a mobile device;
wherein said outputting includes displaying the at least one of the one or more food identities on the screen with the video stream.

3. The food-recognition method of claim 1, wherein the plurality of frames includes views of the one or more food items taken from different angles, different distances, or a combination thereof.

4. The food-recognition method of claim 1, wherein a frame rate of the video stream is greater than or equal to one frame-per-second.

5. The food-recognition method of claim 1, wherein:
the multiple-object detector includes a first convolutional neural network trained to recognize a plurality of multiple-object classes that includes the predicted multiple-object class;
the classifier includes a second convolutional neural network trained to recognize a plurality of classifier classes that includes the one or more predicted classifier classes; and
said determining is based on a hierarchical tree, each of the plurality of classifier classes forming one leaf node of the hierarchical tree.

6. The food-recognition method of claim 5, wherein the number of classifier classes is greater than the number of multiple-object classes.

7. The food-recognition method of claim 5, wherein said determining includes setting the food identity equal to a top predicted classifier class, of the one or more predicted classifier classes, if the top predicted classifier class is a child of the predicted multiple-object class in the hierarchical tree, the top predicted classifier class having a largest classifier probability of the one or more classifier probabilities.

8. The food-recognition method of claim 7, further comprising outputting the largest classifier probability as a confidence level for the food identity.

9. The food-recognition method of claim 7, wherein said determining further includes, if the top predicted classifier class is not a child of the predicted multiple-object class:
identifying, in the hierarchical tree, a plurality of leaf-node descendants of a parent node that are different from the predicted multiple-object class;
summing probabilities of the plurality of leaf-node descendants to obtain a parent probability;
setting the food identity equal to the parent if the parent probability is greater than the multiple-object probability; and
setting the food identity equal to the predicted multiple-object class if the parent probability is less than the multiple-object probability.

10. The food-recognition method of claim 9, further comprising:
outputting the parent probability as a confidence level for the food identity if the parent probability is greater than the multiple-object probability; and
outputting the multiple-object probability as the confidence level for the food identity if the parent probability is less than the multiple-object probability.

11. The food-recognition method of claim 1, further comprising calculating a confidence level for each of the one or more food identities determined from said each frame; and
said creating includes inserting, into the frame list, each of the one or more food identities whose confidence level is greater than a threshold.

12. The food-recognition method of claim 1, wherein:
the food-recognition method further includes counting, for each food identity of the one or more food identities in the updated most-viewed queue, a number of elements for said each food identity in the updated most-viewed queue, the number of elements representing the number of consecutive frames within which said each food identity appears; and
said outputting includes outputting the one of the one or more food identities in the updated most-viewed queue having the greatest number of elements.

13. The food-recognition method of claim 12, further comprising dequeuing an element from the most-viewed queue when a size of the most-viewed queue exceeds a threshold.

14. A food-recognition system, comprising:
a processor;
a memory communicably coupled to the processor;
a food-recognition engine comprising a multiple-object detector and a classifier, the food-recognition engine being implemented as machine-readable instructions that are stored in the memory and, when executed by the processor, control the food-recognition system to:
input each frame, of a plurality of frames of a video stream, into the multiple-object detector to obtain (i) a bounding box identifying where each food item, of one or more food items, appears within said each frame, and (ii) a predicted multiple-object class identifying said each food item with a multiple-object probability, and
for each bounding box:
(i) crop said each frame into a cropped frame based on said each bounding box,
(ii) input the cropped frame into the classifier to obtain a one or more predicted classifier classes that identify said each food item with corresponding one or more classifier probabilities, and (iii) determine a food identity of said each food item based on the predicted multiple-object class, the multiple-object probability, the one or more predicted classifier classes, and the corresponding one or more classifier probabilities, and a time sequencer implemented as machine-readable instructions that are stored in the memory and, when executed by the processor, control the food-recognition system to:

create a frame list of the one or more food identities determined from said each frame, enqueue at least one of the one or more food identities in the frame list into a most-viewed queue of elements to create an updated most-viewed queue, and output at least one of the one or more food identities in the updated most-viewed queue.

15. The food-recognition system of claim 14, wherein:
the food-recognition system further comprises a screen communicably coupled to the processor; and
the food-recognition engine includes additional machine-readable instructions that, when executed by the processor, control the food-recognition system to:
display the video stream on the screen, and
display the at least one of the one or more food identities on the screen with the video stream.

16. The food-recognition system of claim 14, wherein the plurality of frames includes views of the one or more food items taken from different angles, different distances, or a combination thereof.

17. The food-recognition system of claim 14, wherein:
the food-recognition system further comprises a video camera communicably coupled to the processor; and
the food-recognition engine includes machine-readable instructions that, when executed by the processor, control the food-recognition system to capture the video stream from the video camera at a frame rate greater than or equal to one frame-per-second.

18. The food-recognition system of claim 14, wherein:
the multiple-object detector includes a first convolutional neural network trained to recognize a plurality of multiple-object classes that includes the predicted multiple-object class;
the classifier includes a second convolutional neural network trained to recognize a plurality of classifier classes that includes the one or more predicted classifier classes;
the memory further stores a hierarchical tree, each of the plurality of classifier classes forming one leaf node of the hierarchical tree; and
the machine-readable instructions that, when executed by the processor, control the food-recognition system to determine the food identity include machine-readable instructions that, when executed by the processor, control the food-recognition system to determine the food identity based on the hierarchical tree.

19. The food-recognition system of claim 18, wherein the number of classes in the second plurality of classes is greater than the number of classes in the first plurality of classes.

20. The food-recognition system of claim 18, wherein the machine-readable instructions that, when executed by the processor, control the food-recognition system to determine the food identity include machine-readable instructions that, when executed by the processor, control the food-recognition system to set the food identity equal to a top predicted class, of the one or more predicted classifier classes, if the top predicted classifier class is a child of the predicted multiple-object class in the hierarchical tree, the top predicted classifier class having a largest classifier probability of the one or more classifier probabilities.

21. The food-recognition system of claim 20, the food-recognition engine including additional machine-readable instructions that, when executed by the processor, control the food-recognition system to output the largest classifier probability as a confidence level for the food identity.

22. The food-recognition system of claim 20, wherein the machine-readable instructions that, when executed by the processor, control the food-recognition system to determine the food identity include additional machine-readable instructions that, when executed by the processor, control the food-recognition system to:
identify, in the hierarchical tree, a plurality of leaf-node descendants of a parent node that is different from the predicted multiple-object class,
sum probabilities of the plurality of leaf-node descendants to obtain a parent probability,
set the food identity equal to the parent if the parent probability is greater than the multiple-object probability, and
set the food identity equal to the predicted multiple-object class if the parent probability is less than the multiple-object probability.

23. The food-recognition system of claim 22, the food-recognition engine including additional machine-readable instructions that, when executed by the processor, control the food-recognition system to:
output the parent probability as a confidence level for the food identity if the parent probability is greater than the multiple-object probability, and
output the multiple-object probability as the confidence level for the food identity if the parent probability is less than the multiple-object probability.

24. The food-recognition system of claim 15, wherein:
the time sequencer includes additional machine-readable instructions that, when executed by the processor, control the food-recognition system to calculate a confidence level for each of the food identities determined from said each frame; and
the machine-readable instructions that, when executed by the processor, control the food-recognition system to create a frame list include machine-readable instructions that, when executed by the processor, control the food-recognition system to insert, into the frame list, each of the one or more food identities whose confidence level is greater than a threshold.

25. The food-recognition system of claim 15, wherein:
the time sequencer includes additional machine-readable instructions that, when executed by the processor, control the food-recognition system to count, for each food identity of the one or more food identities in the updated most-viewed queue, a number of elements for said each food identity in the updated most-viewed queue, the number of elements representing the number of consecutive frames within which said each food identity appears; and
the machine-readable instructions that, when executed by the processor, control the food-recognition system to output include machine-readable instructions that, when executed by the processor, control the food-recognition system to output the one of the one or more food identities in the updated most-viewed queue having the greatest number of elements.

26. The food-recognition system of claim 25, wherein the time sequencer includes additional machine-readable instructions that, when executed by the processor, control the food-recognition system to dequeue an element from the most-viewed queue when a size of the most-viewed queue exceeds a threshold.

* * * * *